US006589987B2

(12) United States Patent
Kennedy

(10) Patent No.: US 6,589,987 B2
(45) Date of Patent: *Jul. 8, 2003

(54) METHOD OF TREATING CANCER USING TETRAETHYL THIURAM DISULFIDE

(75) Inventor: Thomas Preston Kennedy, Charlotte, NC (US)

(73) Assignee: Charlotte-Mecklenburg Hospital Authority, Charlotte, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/392,122

(22) Filed: Sep. 8, 1999

(65) Prior Publication Data

US 2003/0065026 A1 Apr. 3, 2003

Related U.S. Application Data

(60) Provisional application No. 60/099,390, filed on Sep. 8, 1998.

(51) Int. Cl.$^7$ ........................ A61K 31/27; A61K 31/30; A61K 33/34
(52) U.S. Cl. ........................ 514/491; 514/499; 424/638
(58) Field of Search ................................ 514/491, 499; 424/638

(56) References Cited

U.S. PATENT DOCUMENTS

| | | |
|---|---|---|
| 4,148,885 A | 4/1979 | Renoux et al. |
| 4,426,372 A | 1/1984 | Borch |
| 4,581,224 A | 4/1986 | Borch |
| 4,594,238 A | 6/1986 | Borch |
| 4,645,661 A | 2/1987 | Schonbaum |
| 4,762,705 A | 8/1988 | Rubin |
| 5,035,878 A | 7/1991 | Borch et al. |
| 5,187,193 A | 2/1993 | Borch et al. |
| 5,380,747 A | 1/1995 | Medford et al. |
| 5,679,777 A | 10/1997 | Anderson et al. |
| 5,750,351 A | 5/1998 | Medford et al. |
| 5,759,517 A | 6/1998 | Anderson et al. |
| 5,773,209 A | 6/1998 | Medford et al. |
| 5,773,231 A | 6/1998 | Medford et al. |
| 5,783,596 A | 7/1998 | Medford et al. |
| 5,786,344 A | 7/1998 | Ratain et al. |
| 5,792,787 A | 8/1998 | Medford et al. |
| 6,156,794 A | 12/2000 | Faiman et al. |

FOREIGN PATENT DOCUMENTS

| | | |
|---|---|---|
| GB | 2 081 094 A | 2/1982 |
| JP | 4202139 A | 7/1992 |
| WO | WO 99/34763 | 7/1999 |
| WO | WO 99/34784 | 7/1999 |

OTHER PUBLICATIONS

Rotstein et al., Carcinogenesis (London) (1988), 9(9), 1547–51 Abstract only.*
*Protective Effects of Glutathione on Diethyldithiocarbamate(DDC) Cytotoxicity: A Possible Mechanism*, L. D. Trombetta et al., Toxicology and Applied Pharmacology 93, pp. 154–164, 1988.
*Disulfiram and Tumor Inhibition*, H. K. A. Schirmer et al., Transactions of American Association of Genito–Urinary Surgeons, vol. 58, pp. 63–66, 1966.
*Inhibition of Meth–A Tumor Cell Proliferation in Combined Use of Disulfiram with Catalase*, H. Mashiba et al., Toxicology Letters, 61, pp. 75–80, 1992.
*Phase I Study of the Combination of Disulfiram with Cisplatin*, D. J. Stewart et al., Am. J. Clin. Oncol. (CCT), vol. 10, No. 6, pp. 517–519, 1987.
*Antitumour Activity of New Nitrosources on Yoshida Sarcoma Ascites Cells In Vivo*, M. Habs et al., Institute of Toxicology and Chemotherapy, German Cancer Research Center, Heidelberg, FRG, pp. 438–444.
*A Review of the Modulation of Cisplatin Toxicities by Chemoprotectants*, R. T. Dorr, Platinum and Other Metal Coordination Compounds in Cancer Chemotherapy, pp. 131–154, 1996.
*Cytotoxic Interactions of $Zn^{2+}$ In Vitro: Melanoma Cells Are More Susceptible Than Melanocytes*, J. Borovansky et al., Melanoma Research, vol. 7, pp. 449–453, 1997.
Dobel, et al.; "Dithiocarbamates Induces Apoptosis in Thymocytes by Raising the Intracellular Level of Redox–active Copper", *The Journal of Biological Chemistry*, vol. 270, No. 44, Nov. 3, pp. 26202–26208, 1995.
Johansson; "A review of the pharmacokinetics and pharmacodynamics of disulfiram and its metabolites", *Acta Psychiatr Scand*, 1992: 86: pp. 15–26.
Arnelle et al.; "Diethyl Dithiocarbamate–Induced Decomposition of S–Nitrosothiols", *nitric oxide: biology and Chemistry*; Feb., pp. 56–64 (1997).
Verhaegh et al.; "Regulation of p53 by Metal Ions and by Antioxidants: Dithiocarbamate Down–Regulates p53 DNA–Binding Activity by Increasing the Intracellular Level of Copper"; *Molecular and Cellular Biology*, vol. 17, No. 10, Oct. 1997, pp. 5699–5706.
Schreck et al.; "Dithiocarbamates as Potent Inhibitors of Nuclear Factor κB Activation in Intact Cells"; *J Exp. Med.*, vol. 175, May 1992, pp.1181–1194.
Burns, et al.; "1,1–Dithiolato Complexes of the Transition Elements", *Advances in Inorganic Chemistry and Radiochemistry*, vol. 23, pp. 211–280. (1980).

* cited by examiner

Primary Examiner—Jerome D. Goldberg
(74) Attorney, Agent, or Firm—Alston & Bird LLP

(57) ABSTRACT

Dithiocarbamate, particularly tetraethylthiuram disulfide strongly inhibits the growth of cancer cells of a variety of cell types. Such inhibitory effect is enhanced by heavy metal ions such as copper ions, cytokines and ceruloplasmin. A method is presented for using tetraethylthiuram disulfide to reduce tumor growth, and to potentiate the effect of other anticancer agents.

6 Claims, 12 Drawing Sheets

METHOD OF TREATING CANCER USING TETRAETHYL THIURAM DISULFIDE

CROSS-REFERENCE TO RELATED APPLICATIONS

This application claims prior §119(e) to Provisional U.S. Application Serial No. 60/099,390 file date Sep. 8, 1998 the entirety of which is incorporated herein by reference.

FIELD OF INVENTION

This invention generally relates to methods of treating cancer, and particularly to methods of treating cancer using dithiocarbamate.

BACKGROUND OF THE INVENTION

Cancer, the uncontrolled growth of malignant cells, is a major health problem of the modern medical era and ranks second only to heart disease as a cause of death in the U.S. While some malignancies, such as adenocarcinoma of the breast and lymphomas such as Hodgkins Disease, respond relatively well to current chemotherapeutic antineoplastic drug regimens, other cancers are poorly responsive to chemotherapy, especially non-small cell lung cancer and pancreatic, prostate and colon cancers. Even small cell cancer of the lung, initially chemotherapy sensitive, tends to return after remission, with widespread metastatic spread leading to death of the patient. Thus, better treatment approaches are needed for this illness. Also, because almost all currently available antineoplastic agents have significant toxicities, such as bone marrow suppression, renal dysfunction, stomatitis, enteritis and hair loss, it would be of major advantage to have a relatively less toxic agent available for use alone or in combination with current drugs in order to better treat the patient without risking injury from the therapy itself.

Recently, dithiocarbamates containing a reduced sulfhydryl group, e.g., pyrrolidinedithiocarbamate, (PDTC) have been shown to inhibit the proliferation of cultured vascular smooth muscle cells as well as cultured colorectal cancer cells. See, e.g, Tsai et al., *J. Biol. Chem.* 271:3667–3670 (1996); Chinery et al., *Nature Med.* 11: 1233–1241 (1997); Chinery et al., *Cancer Res.* 58:2323–2327 (1998). It has been suggested that antioxidants having a reduced sulfhydryl group may be used in treating colorectal cancer.

Dithiocarbamates such as pyrrolidinedithiocarbamate (PDTC) and diethyldithiocarbamate (DEDC) have also been reported to inhibit apoptosis in different cell types, e.g., in rat thymocytes and Jurkat T lymphocytes, in short-term incubations. See, e.g. Nobel et al. *Chem. Res. Toxicol.* 10(6):636–643 (1997). In this article, it is disclosed that copper is required in the inhibition of apoptosis by PDTC and DEDC. It is also disclosed that thiuram disulfides such as disulfiram (oxidized disulfide of diethyldithiocarbamate which does not contain a reduced sulfhydryl group) are much more potent apoptosis inhibitors than PDTC or DEDC. In addition, as compared to the reduced molecules, disulfiram inhibition of thymocyte apoptosis is not dependent on copper.

In another report, it is however reported that upon long-term incubation with rat thymocytes, both the reduced dithiocarbamates and their disulfides are capable of inducing apoptosis. See Burkitt et al. *Arch. Biochem. Biophysics* 353(1):73–84 (1998). However, reduced dithiocarbamates requires copper, while the thiuram disulfide induction of apoptosis is essentially not affected by the removal of copper ions. It is suggested that copper ions are required for oxidizing dithiocarbamates to thiuram disulfides but not required for the apoptosis-inducing effect of thiuram disulfides. See Nobel et al. *J. Biol. Chem.* 270:26202–26208 (1995); Burkitt et al. *Arch. Biochem. Biophysics* 353(1):73–84 (1998).

The antioxidant effect of disulfiram has also been studied in the art. Rao et al. *Jpn. J. Cancer Res.* 80(12) 1171–5 (1989) examines the effect of disulfiram on transmammary carcinogenesis induction in mice by anthracene. It is disclosed that tumor incidence associated with anthracene is lower in nursing mother mice pretreated with disulfiram than those untreated. It is suggested that disulfiram can counteract the effect of carcinogen anthracene and thus inhibiting transmammary carcinogenesis in mice.

Mashiba et al. *Toxicol.* Lett. 61(1):75–80 (1992) discloses that the combined use of disulfiram with the antioxidant enzyme catalase induces inhibition of cell proliferation. It is suggested that the antiproliferation effect is due to the formation of compounds or metabolites with cytostatic activity as a result of the reaction of disulfiram with catalase.

Mashiba et al. *Jpn J. Exp. Med.* 60(4):209–14 (1990) studies the roles of oxygen free radicals in the inhibition of tumor cell proliferation. Disulfiram is used as a metal chelator to inactivate superoxide dismutase. Ascorbic acid is employed to inhibit catalase. It is disclosed that Meth A tumor cell proliferation is inhibited upon simultaneous addition of disulfiram and ascorbic acid. It is suggested that the combined use of disulfiram and ascorbic acid increases the intracellular oxygen free radicals within tumor cells.

SUMMARY OF THE INVENTION

The present invention provides a method for treating established cancer using disulfiram, either alone, or in combination with a heavy metal ion or a stimulant of a heavy metal ion.

It has been discovered that thiuram disulfide alone exhibits potent inhibitory effect on established tumor cells in absence of catalase or ascorbic acid. Disulfiram is even effective in inhibiting the growth of established melanomas cells and non-small cell lung cancer cells, which are known to be poorly responsive to currently available antineoplastic agents.

In addition, in contrast to the prior art teachings discussed above, it has further been surprisingly discovered that the antiproliferative and antineoplastic effect of disulfiram on established tumor cells is heavy metal ion-dependent. Further, the tumor cell growth inhibition effect of disulfiram can be significantly enhanced by the addition of heavy metal ions such as copper, zinc, gold, and silver ions, or a heavy metal ion stimulant, e.g., ceruloplasmin or a cytokine which can induce an acute phase response in the tumor cells.

Accordingly, this invention provides a method for treating established cancer in a patient by administering to the patient a therapeutically effective amount of a thiuram disulfide. Advantageously, a tetralkylthiuram disulfide such as tetraethylthiuram disulfide, better known as disulfiram is used.

In accordance with another aspect of this invention, a method for treating established cancer in a patient is provided comprising administering to the patient a therapeutically effective amount of a thiuram disulfide, preferably disulfiram, and a heavy metal ion. In a preferred embodiment, the heavy metal ion is administered as a complex or chelate with the thiuram disulfide. Suitable heavy metal ions include but are not limited to ions of arsenic, bismuth, cobalt, copper, chromium, gallium, gold, iron, manganese, nickel, silver, titanium, vanadium, selenium, and zinc. In another preferred embodiment, the thiuram disulfide and the heavy metal ion are administered in combination with another anticancer agent.

In accordance with another aspect of this invention, a method for treating established cancer in a patient is provided which comprises administering to the patient a therapeutically effective amount of a thiuram disulfide and a cytokine such as interferon α, interferon β, interferon γ, and IL-6. Advantageously, the thiuram disulfide administered is a tetraalkyl thiuram disulfide, preferably disulfiram. In addition, another anticancer agent can also be administered to the patient for a combination therapy.

In accordance with yet another aspect of this invention, the method for treating established cancer in a patient comprises administering to the patient a therapeutically effective amount of a thiuram disulfide, preferably disulfiram, and ceruloplasmin.

In addition, the present invention provides a pharmaceutical composition which comprises a pharmaceutically acceptable carrier, and a complex between a thiuram disulfide and a heavy metal ion. Optionally, the composition can further contain another anticancer agent.

The active compounds of this invention can be administered through a variety of administration routes. For example, they can be administered orally, intravenously, indermally, subcutaneously and topically.

The present invention is effective for treating various types of cancer, including but not limited to melanoma, non-small cell lung cancer, small cell lung cancer, renal cancer, colorectal cancer, breast cancer, pancreatic cancer, gastric cancer, bladder cancer, ovarian cancer, uterine cancer, lymphoma, and prostate cancer. In particular, the present invention will be especially effective in treating melanoma, lung cancer, breast cancer, and prostate carcinoma.

Thiuram disulfides such as disulfiram have been used clinically for many years in treating various other diseases such as alcohol abuse, and have been proved to be relatively non-toxic and safe. (Disulfiram is available as an oral formulation in the U.S. as Antabuse® from Wyeth-Ayerst Laboratories, Philadelphia, Pa.). Thus, the use of thiuram disulfides in this invention offers a readily available and easily used treatment for cancers in man and other mammals.

BRIEF DESCRIPTION OF THE DRAWINGS

FIG. 5A shows that disulfiram plus copper reduce expression of the cell-cycle protein cyclin A.

DETAILED DESCRIPTION OF THE INVENTION

Figure 1A:
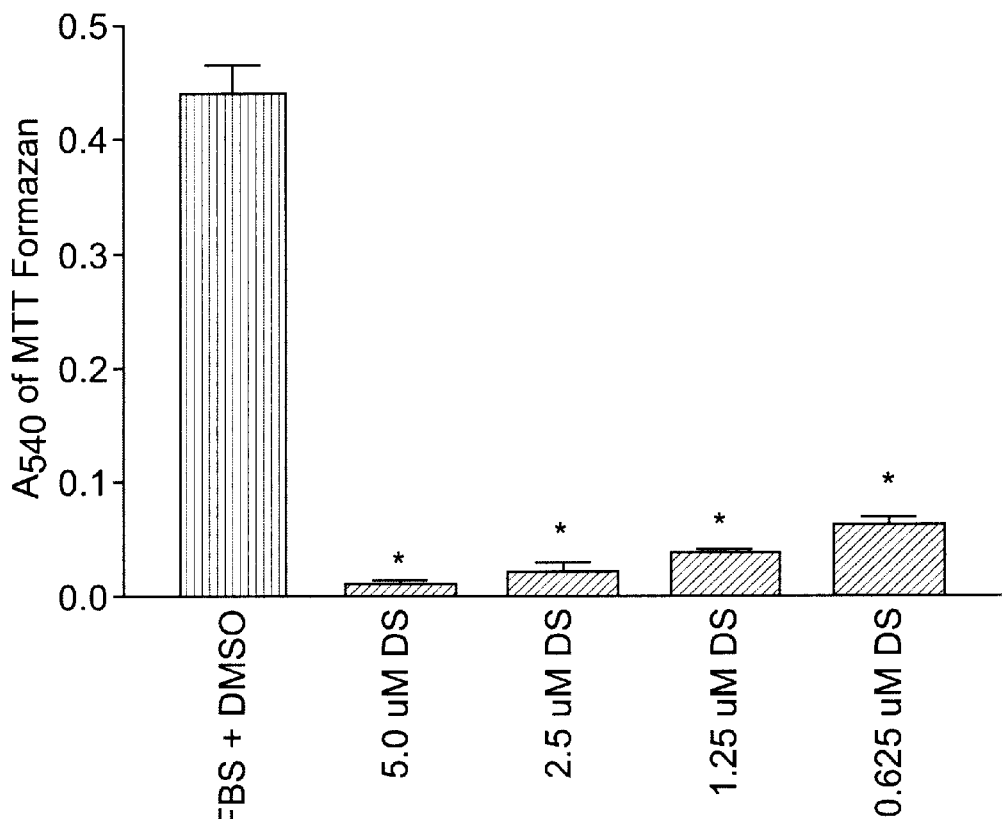
FIG. 1A shows that disulfiram inhibits proliferation of M1619 human melanoma cell lines.

The present invention now will be described more fully hereinafter with reference to the accompanying examples, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "thiuram disulfides" refers to compounds having the formula of:

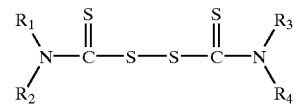

where $R_1$, $R_2$, $R_3$, and $R_4$ are same or different and represent hydrogen, and unsubstituted or substituted alkyl, alkenyl, alkynyl, aryl, alkoxy, and heteroaryl groups. It is noted that the alkyl groups can include cycloalkyl and hetercycloalkyl groups. $R_1$, $R_2$, and the N atom in the formula can together form an N-heterocyclic ring, which is, e.g., heterocycloalkyl or heterocycloaryl. Likewise, $R_3$, $R_4$ and the N atom in the formula can together form an N-heterocyclic ring, which is, e.g., heterocycloalkyl or heterocycloaryl. Typically, $R_1$ and $R_2$ are not both hydrogen, and $R_3$ and $R_4$ are not both hydrogen. Thus, thiuram disulfide is a disulfide form of dithiocarbamates which have a reduced sulfhydryl group. Many dithiocarbamates are known and synthesized in the art. Nonlimiting examples of dithiocarbamates include diethyldithiocarbamate, pyrrolidinedithiocarbamate, N-methyl, N-ethyldithiocarbamates, hexamethylenedithiocarbamate, imadazolinedithiocarbamates, dibenzyldithiocarbamate, dimethylenedithiocarbamate, dipopyldithiocarbamate, dibutyldithiocarbamate, diamyldithiocarbamate, N-methyl, N-cyclopropylmethyldithiocarbamate, cyclohexy-lamyldithiocarbamate pentamethylenedithiocarbamate, dihydroxyethyldithiocarbamate, N-methylglucosamine dithiocarbamate, and salts and derivatives thereof. Typically, a sulfhydryl-containing dithiocarbamate can be oxidized to form a thiuram disulfide.

Any pharmaceutically acceptable form of thiuram disulfides as defined above can be used. For example, tetraalkylthiuram disulfide, preferably tetraethylthiuram disulfide which is known as disulfiram, is used in the method of this invention. Disulfiram has the following formula:

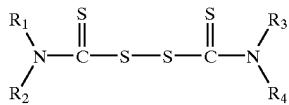

where $R_1$, $R_2$, $R_3$, and $R_4$ are all ethyl. Disulfiram has been used clinically in the treatment of alcohol abuse, in which disulfiram inhibits hepatic aldehyde dehydrogenase. Methods of making thiuram disulfides are generally known in the art. Exemplary methods are disclosed in, e.g., Thorn, et al., *The Dithiocarbamates and Related Compounds*, Elsevier, N.Y., 1962; and U.S. Pat. Nos. 5,166,387, 4,144,272, 4,066,697, 1,782,111, and 1,796,977, all of which are incorporated herein by reference.

The term "treating cancer" as used herein, specifically refers to administering therapeutic agents to a patient diagnosed of cancer, i.e., having established cancer in the patient, to inhibit the further growth or spread of the malignant cells in the cancerous tissue, and/or to cause the death of the malignant cells.

This invention provides a method for treating cancer in a patient. In accordance with the present invention, it has been discovered that thiuram disulfides such as disulfiram, can inhibit the growth of tumor cells in a heavy metal ion-dependent manner. Specifically, heavy metal ions such as copper, zinc, gold, and silver ions significantly enhance the inhibitory effect of thiuram disulfides on tumor cells, while the depletion of such heavy metal ions prevents growth inhibition by disulfiram.

Accordingly, in accordance with one aspect of this invention, a method for treating an established cancer in a patient is provided. A thiuram disulfide can be administered to a patient having established cancer to treat the cancer. Preferably, the thiuram disulfide administered is a tetra alkyl thiuram disulfide such as tetra ethylthiuram disulfide, i.e., disulfiram.

In another aspect of this invention, the method for treating cancer in a patient comprises administering to the patient a therapeutically effective amount of a thuram disulfide and a heavy metal ion.

Non-limiting examples of heavy metal ions include ions of arsenic, bismuth, cobalt, copper, chromium, gallium, gold, iron, manganese, nickel, silver, titanium, vanadium, selenium and zinc. Preferably, gold, silver, zinc, selenium and copper ions are used. Sources of such heavy metal ions are known to the ordinary artisan. For example, such ions can be provided in a sulfate salt, or chloride salt form, or any other pharmaceutically suitable forms.

One or more thiuram disulfide compounds and one or more heavy metal ions can be administered to a patient. The thiuram disulfide compound and the heavy metal ion can be administered in combination or separately. Preferably, they are administered as a chelating complex. As is known in the art, thiuram disulfide compounds are excellent chelating agents and can chelate heavy metal ions to form chelates. Preparation of chelates of thiuram disulfide compounds and heavy metal ions are known to the ordinary artisan. For example, chelates of disulfiram and copper, zinc, silver, or gold ions can be conveniently synthesized by mixing, in a suitable solvents, disulfiram with, e.g., $CuSO_4$, $ZnCl_2$, $C_3H_5AgO_3$, or $HAuCl_4 3H_2O$ to allow chelates to be formed. Other thiuram disulfide compound-heavy metal ion chelates are disclosed in, e.g., Burns et al., *Adv. Inorg. Chem. Radiochem.* 23:211–280 (1980), which is incorporated herein by reference.

In accordance with another aspect of this invention, a method for treating cancer in a patient is provided which includes administering to the patient a therapeutically effective amount of a thiuram disulfide compound and an intracellular heavy metal ion stimulant, which can enhance the intracellular level of the above described heavy metal ions in the patient.

Intracellular heavy metal ion carriers are known. For example, ceruloplasmin can be administered to the patient to enhance the intracellular copper level. Other heavy metal ion carriers known in the art may also be administered in accordance with this aspect of the invention. The heavy metal ion carriers and the thiuram disulfide compound can be administered together or separately, and preferably in separate compositions.

Ceruloplasmin is a protein naturally produced by human body and can be purified from human serum. This 132-kD glycoprotein, which carries 7 copper atoms complexed over three 42–45 kD domains, is an acute phase reactant and the major copper-carrying protein in human plasma. See Halliwell, et al. *Methods Enzymol.* 186:1–85(1990). When transported into cells, at least some of the bound cupric ions can be accessible for complexation with the thiuram disulfide compound administer to the patient. Percival, et al. *Am. J. Physiol.* 258:3140–3146 (1990).

Ceruloplasmin can be isolated from animal or human serum. Alternatively, genetical engineered ceruloplasmin can also be expressed in vitro in, e.g., bacteria, yeast, plant, animal or human cells and purified therefrom. Ceruloplasmin and thiuram disulfide are typically administered in different compositions. Thiuram disulfide and ceruloplasmin can be administered at about the same time, or at some time apart. For example, ceruloplasmin can be administered from about five minutes to about 12 hours before or after thiuram disulfide is administered to the patient.

In another embodiment, instead of heavy metal ion carriers, a cytokine is administered to the patient in addition to a thiuram disulfide compound. Suitable cytokines include, e.g., interferon α, interferon β, interferon γ, and interleukin 6 (IL-6). Such cytokines, when administered to a patient, are capable of inducing an acute phase response in the body of the patient thus stimulating serum ceruloplasmin in the patient.

The biochemical and physiological properties of such cytokines have been studied extensively in the art and are familiar to skilled artisans. The cytokines can be purified from human or animal serum. They can also be obtained by genetic engineering techniques. In addition, commercially available samples of the above-identified cytokines may also be used in this invention. Genetically or chemically modified cytokines can also be administered. For example, it is known that certain peptidic cytokines have longer circulation time in animals when such cytokines are conjugated with a water soluble, non-immunogenic polymer such as polyethylene glycol.

Typically the cytokines are administered in a different composition from the thiuram disulfide compound. The cytokines and thiuram disulfide can be administered at about the same time, or at some time apart from each other. For example the cytokines can be administered from about 5 minutes to about 24 hours before or after the administration of thiuram disulfide.

In accordance with another aspect of this invention, the method of this invention can be used in combination with a conventional anticancer therapy. For example, the method of this invention can be complemented by a conventional radiation therapy or chemotherapy. Thus, in one embodiment of this invention, the method of this invention comprises administering to a patient a thiuram disulfide compound and heavy metals, and another anticancer agent. Treatment by ceruloplasmin or a cytokine, and a thiuram disulfide compound can also be conducted along with the treatment with another anticancer agent.

Any anticancer agents known in the art can be used in this invention so long as it is pharmaceutically compatible with the thiuram disulfide compounds, heavy metal ions, ceruloplasmin, and/or cytokines used. By "pharmaceutically compatible" it is intended that the other anticancer agent will not interact or react with the above composition, directly or indirectly, in such a way as to adversely affect the effect of the treatment of cancer, or to cause any significant adverse side reaction in the patient.

Exemplary anticancer agents known in the art include cisplatin, carmustine, herceptin, carboplatin, cyclophosphamide, nitrosoureas, fotemustine, vindesine, etoposide, daunorubicin, adriamycin, taxol, taxotere, fluorouracil, methotrexate, melphalan, bleomycin, salicylates, aspirin, piroxicam, ibuprofen, indomethacin, maprosyn, diclofenac, tolmetin, ketoprofen, nabumetone, oxaprozin, doxirubicin, nonselective cyclooxygenase inhibitors such as nonsteroidal anti-inflammatory agents (NSAIDS), and selective cyclooxygenase-2 (COX-2) inhibitors.

The anticancer agent used can be administered simultaneously in the same pharmaceutical preparation with the thiuram disulfide compound, heavy metal ions, ceruloplasmin, and/or cytokines as described above. The anticancer agent can also be administered at about same time but by a separate administration. Alternatively, the anticancer agent can be administered at a different time from the administration of the thiuram disulfide compound, heavy metal ions, ceruloplasmin, and/or cytokines. Some minor degree of experimentation may be required to determine the best manner of administration, this being well within the capability of one skilled in the art once apprised of the present disclosure.

The methods of this invention are suitable for treating cancers in animals, especially mammals such as canine, bovine, porcine, and other animals. Advantageously, the methods are used in treating human patients. The methods are useful for treating various types of cancer, including but not limited to melanoma, non-small cell lung cancer, small cell lung cancer, renal cancer, colorectal cancer, breast cancer, pancreatic cancer, gastric cancer, bladder cancer, ovarian cancer, uterine cancer, lymphoma, and prostate cancer. In particular, the present invention will be especially effective in treating melanoma, lung cancer, breast cancer, and prostate carcinoma.

The active compounds of this invention are typically administered in a pharmaceutically acceptable carrier through any appropriate routes such as parenteral, intravenous, oral, intradermal, subcutaneous, or topical administration. The active compounds of this invention are administered at a therapeutically effective amount to achieve the desired therapeutic effect without causing any serious adverse effects in the patient treated.

The thiuram disulfide compound disulfiram can be effective when administered at an amount within the conventional clinical ranges determined in the art. Typically, it can be effective at an amount of from about 125 to about 1000 mg per day, preferably from about 250 to about 500 mg per day. However, the amount can vary with the body weight of the patient treated. The active ingredient may be administered at once, or may be divided into a number of smaller doses to be administered at predetermined intervals of time. The suitable dosage unit for each administration of disulfiram can be, e.g., from about 50 to about 1000 mg, preferably from about 250 to about 500 mg. The desirable peak plasma concentration of disulfiram generally is about 0.05 to about 10 $\mu$M, preferably about 0.5 to about 5 $\mu$M, in order to achieve a detectable therapeutic effect. However, a plasma concentration beyond such ranges may work as well.

Disulfiram has been used clinically in treating alcohol abuse. A dosage form of disulfiram approved by the U.S. Food and Drug Administration (Antabuseo®) can be purchased in 250 and 500 mg tablets for oral administration from Wyeth-Ayerst Laboratories (P.O. Box 8299, Philadelphia, Pa. 19101, Telephone 610–688–4400).

Disulfiram implanted subcutaneously for sustained release has also been shown to be effective at an amount of 800 to 1600 mg to achieve a suitable plasma concentration. This can be accomplished by using aseptic techniques to surgically implant disulfiram into the subcutaneous space of the anterior abdominal wall. See, e.g., Wilson et al., *J. Clin. Psych.* 45:242–247 (1984).

A sustained release dosage formulation comprised to 80% poly(glycolic-co-L-lactic acid) and 20% disulfiram has also been described in Phillips et al., *J. Pharmaceut. Sci.* 73:1718–1720 (1984).

The pharmacology and toxicology of Antabuse® are detailed in Physicians Desk Reference, 50th edition, Medical Economics, Montvale, N.J., pages 2695–2696. Steady-state serum levels of approximately 1.3 $\mu$M have been measured in humans taking repeated doses of 250 mg disulfiram daily. See, e.g., Faiman et al., *Clin. Pharmacol. Ther.* 36:520–526 (1984); and Johansson, *Acta Psychiatr. Scand.*, Suppl. 369:15–26 (1992). Disulfiram is relatively non-toxic, with an $LD_{50}$ in rodents of 8.6 g/kg. See, e.g., *The Merck Index*, 10th Edition, Reference 3382, Merck & Co., Rahway, N.J., 1983, page 491.

Disulfiram can be used in a similar dosage in the present invention. The therapeutically effective amount for other thiuram disulfide compounds may also be estimated or calculated based on the above dosage ranges of disulfiram and the molecular weights of disulfiram and the other thiuram disulfide compounds, or by other methods known in the art.

Heavy metal ions can be administered separately as an aqueous solution in a pharmaceutically suitable salt form. However, they are preferably administered in a chelate form in which the ions are complexed with thiuram disulfide compounds. Thus, the amount of heavy metal ions to be used advantageously is proportional to the amount of thiuram disulfide compound to be administered based on the molar ratio between a heavy metal ion and thiuram disulfide compound in the chelate. Methods for preparing such chelates or complexes are known and the preferred methods are disclosed above and in the examples below.

The therapeutically effective amount for IL-6 can be from about 1 to about 100 μg/kg per day, preferably from about 5 to about 50 μg/kg per day. Interferon α can be administered at from about $0.1 \times 10^6$ to about $10 \times 10^6$ international units per day, preferably from about 3 to about $8 \times 10^6$ international units per day, and the administration frequency can be from about three times per week to about once per day. Suitable dosage for interferon β can range from about 1 to about 200 μg per day, preferably from about 10 to about 100 μg per day administered once per week up to once per day. Interferon γ can be administered at a dosage of from about 1 to about 1000 μg per day, preferably from about 50 to about 250 μg per day. Ceruloplasmin may be administered at an amount of from about 1 to about 100 mg per day, preferably from about 5 to about 30 mg per day.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can also be adjusted as the various factors change over time.

The active compounds of this invention can be administered to a patient to be treated through any suitable routes of administration.

Advantageously, the active compounds are delivered to the patient parenterally, i.e., intravenously or intramuscularly. For parenteral administration, the active compounds can be formulated into solutions or suspensions, or in lyophilized forms for conversion into solutions or suspensions before use. Sterile water, physiological saline, e.g., phosphate buffered saline (PBS) can be used conveniently as the pharmaceutically acceptable carriers or diluents. Conventional solvents, surfactants, stabilizers, pH balancing buffers, anti-bacteria agents, and antioxidants can all be used in the parenteral formulations, including but not limited to acetates, citrates or phosphates buffers, sodium chloride, dextrose, fixed oils, glycerine, polyethylene glycol, propylene glycol, benzyl alcohol, methyl parabens, ascorbic acid, sodium bisulfite, and the like. The parenteral formulation can be stored in any conventional containers such as vials, ampoules, and syringes.

The active compounds can also be delivered orally in enclosed gelatin capsules or compressed tablets. Capsules and tablets can be prepared in any conventional techniques. For example, the active compounds can be incorporated into a formulation which includes pharmaceutically acceptable carriers such as excipients (e.g., starch, lactose), binders (e.g., gelatin, cellulose, gum tragacanth), disintegrating agents (e.g., alginate, Primogel, and corn starch), lubricants (e.g., magnesium stearate, silicon dioxide), and sweetening or flavoring agents (e.g., glucose, sucrose, saccharin, methyl salicylate, and peppermint). Various coatings can also be prepared for the capsules and tablets to modify the flavors, tastes, colors, and shapes of the capsules and tablets. In addition, liquid carriers such as fatty oil can also be included in capsules.

Other forms of oral formulations such as chewing gum, suspension, syrup, wafer, elixir, and the like can also be prepared containing the active compounds used in this invention. Various modifying agents for flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered topically through rectal, vaginal, nasal or mucosal applications. Topical formulations are generally known in the art including creams, gels, ointments, lotions, powders, pastes, suspensions, sprays, and aerosols. Typically, topical formulations include one or more thickening agents, humectants, and/or emollients including but not limited to xanthan gum, petrolatum, beeswax, or polyethylene glycol, sorbitol, mineral oil, lanolin, squalene, and the like. A special form of topical administration is delivery by a transdermal patch. Methods for preparing transdermal patches are disclosed, e.g., in Brown, et al., *Annual Review of Medicine*, 39:221–229 (1988), which is incorporated herein by reference.

The active compounds can also be delivered by subcutaneous implantation for sustained release. This may be accomplished by using aseptic techniques to surgically implant the active compounds in any suitable formulation into the subcutaneous space of the anterior abdominal wall. See, e.g., Wilson et al., *J. Clin. Psych.* 45:242–247 (1984). Sustained release can be achieved by incorporating the active ingredients into a special carrier such as a hydrogel. Typically, a hydrogel is a network of high molecular weight biocompatible polymers, which can swell in water to form a gel like material. Hydrogels are generally known in the art. For example, hydrogels made of polyethylene glycols, or collagen, or poly(glycolic-co-L-lactic acid) are suitable for this invention. See, e.g., Phillips et al., *J. Pharmaceut. Sci.* 73:1718–1720 (1984).

The active compounds can also be conjugated, i.e., covalently linked, to a water soluble non-immunogenic high molecular weight polymer to form a polymer conjugate. Advantageously, such polymers, e.g., polyethylene glycol, can impart solubility, stability, and reduced immunogenicity to the active compounds. As a result, the active compound in the conjugate when administered to a patient, can have a longer half-life in the body, and exhibit better efficacy. PEGylated proteins are currently being used in protein replacement therapies and for other therapeutic uses. For example, PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). For a general review of PEG-protein conjugates with clinical efficacy. See, e.g., Burnham, *Am. J. Hosp. Pharm.*, 15:210–218 (1994). Preferably, the covalent linkage between the polymer and the active compound is hydrolytically degradable and is susceptible to hydrolysis under physiological conditions. Such conjugates are known as "prodrugs" and the polymer in the conjugate can be readily cleaved off inside the body, releasing the free active compounds.

Alternatively, other forms controlled release or protection including microcapsules and nanocapsules generally known in the art, and hydrogels described above can all be utilized in oral, parenteral, topical, and subcutaneous administration of the active compounds.

Another preferable delivery form is using liposomes as carrier. Liposomes are micelles formed from various lipids such as cholesterol, phospholipids, fatty acids, and derivatives thereof. Active compounds can be enclosed within such micelles. Methods for preparing liposomal suspensions containing active ingredients therein are generally known in the art and are disclosed in, e.g., U.S. Pat. No. 4,522,811, which is incorporated herein by reference. Several anticancer drugs delivered in the form of liposomes are known in the art and are commercially available from Liposome Inc. of Princeton, N.J., U.S.A. It has been shown that liposomal can reduce the toxicity of the active compounds, and increase their stability.

The active compounds can also be administered in combination with other active agents that treats or prevents another disease or symptom in the patient treated. However, it is to be understood that such other active agents should not interfere with or adversely affect the effects of the active compounds of this invention on the cancer being treated. Such other active agents include but are not limited to antiviral agents, antibiotics, antifungal agents, anti-inflammation agents, antithrombotic agents, cardiovascular drugs, cholesterol lowering agents, hypertension drugs, and the like.

It is to be understood that individuals placed on disulfiram therapy for their cancer must be warned against exposure to alcohol in any form, to avoid the precipitation of nausea and vomiting from buildup of acetaldehyde in the bloodstream. Subjects therefore must not only refrain from ingesting alcohol containing beverages, but should also not ingest over the counter formulations such as cough syrups containing alcohol or even use rubbing alcohol topically.

METHODS

Culture of Malignant Cell Lines. Human malignant cell lines were obtained from American Type Tissue Culture Collection (Rockville, Md.). Melanoma cells lines CRL 1585 and 1619 were cultured in RPMI 1640 (GIBCO-BRL, Life Technologies, Grand Island, N.Y.) with 10% FBS and passed with nonenzymatic Cell Dissociation Solution7 (Sigma). The prostate adenocarcinoma cell line CRL 1435 (PC-3) was also cultured in RPMI 1640 with 10% FBS but passed with 0.05% trypsin and 0.53 mM EDTA. The squamous lung carcinoma NCI-H520 and the adenosquamous lung carcinoma NCI-H596 cell lines were grown in RPMI 1640 supplemented with 10% FBS, 10 mM HEPES and 1.0 mM sodium pyruvate and passed with trypsin/EDTA. The small cell lung carcinoma NCI-H82 was cultured as a suspension in RPMI 1640 with 10% FBS. All of the above were grown in a 37° C. humidified environment containing 5% $CO_2$/air. The breast carcinoma cell line MDA-MB-453 was grown in a 37° C. humidified environment with free gas exchange with atmospheric air using Leibovitz's L-15 medium with 2 mM L-glutamine and 10% FBS and was passed with trypsin/EDTA.

Measurement of Proliferation in Cell Cultures. Proliferation of cultured cells was quantitated using a previously reported colorimetric method based upon metabolic reduction of the soluble yellow tetrazolium dye 3-[4,5-dimethylthiazol]-2yl-2,5-diphenyl tetrazolium bromide (MTT) to its insoluble purple formazan by the action of mitochondrial succinyl dehydrogenase. See Hirst et al. *Am. J. Respir. Cell Mol. Biol.* 7:574–581 (1992); Dashtaki, et al. *J. Pharmacol. Exper. Ther.* 285:876–219 (1998). This assay empirically distinguishes between dead and living cells. For proliferation studies, cells were seeded into 24-well uncoated plastic plates (Costar) at 50,000 cells per well and cultured with respective media and mitogens. After 24–96 hr, medium was removed, cells were washed twice with 1 ml of sterile Dulbecco's modified phosphate buffered saline without $Ca^{2+}$ or $Mg^{2+}$ (DPBS), the medium was replaced with 1 ml/well fresh medium containing 100 µg/ml MTT, and plates were incubated an additional hour. MTT-containing medium was removed, 0.5 ml dimethylsulfoxide (DMSO) was added to each well, and the absorbance of the solubilized purple formazan dye was measured at 540 nm. A total of 4–6 wells was studied at each treatment condition. Preliminary studies were performed with 50–200 µg/ml MTT incubated for 15 min to 3 hr to determine the optimum concentration and incubation time at which the rate of conversion was linear and proportional to the number of cells present. The absorbance of the MTT formazan reduction product ($A_{540}$) correlated with cell numbers counted by hemocytometer with an $R^2$=0.99. In some experiments, the MTT assay and responses to FBS and inhibitors were also confirmed by performing cell counts on 10 random fields/well of Giemsa-modified Wright's stained monolayers viewed at 40 power using a 0.01-$cm^2$ ocular grid.

Cell Culture Treatments. The effect of disulfiram (0.15 to 5.0 µM) and PDTC (0.625 to 5.0 µM) (both from Sigma Chemicals, St. Louis, Mo.) on proliferation of malignant cell lines was studied in cultures stimulated with 10% FBS. Disulfiram was solubilized in dimethylsulfoxide (DMSO) so that the final concentration of DMSO was less than 0.3–0.5%. Equal volumes of DMSO were added to control experiments. Cell numbers were quantitated by the MTT assay 24–72 hours later. In some experiments disulfiram or PDTC were added immediately after cells were plated. In other experiments, cells were plated and allowed to grow for 24–72 hours before fresh media with disulfiram or PDTC was added, and cell numbers were studied by the MTT assay 24–72 hr later. Synergy was studied between disulfiram and N,N'-bis(2-chloroethyl-N-nitrosourea (carmustine or BCNU, 1.0 to 1,000 µM) or cisplatin (0.1 to 100 µg/ml) added to medium. The effect of metals on disulfiram was studied with 0.2 to 10 µM copper (provided as $CuSO_4$), zinc (as $ZnCl_2$), silver (as silver lactate) or gold (as $HAuCl_4 3H_2O$) ions added to growth medium. No pH changes occurred with addition of metal salts to culture medium. To provide a biologically relevant source of copper, in some experiments medium was supplemented with human ceruloplasmin (Sigma) at doses replicating low and high normal adult serum concentrations (250 and 500 µg/ml).

Potential redox effects of disulfiram were studied in three sets of experiments. The importance of cellular glutathione (GSH) in mediating or modulating dithiocarbamate toxicity was studied by measuring levels of intracellular GSH after treatment with disulfiram. Disulfiram (5 µM), with or without 1.6 µM $CuSO_4$, was added to cells grown to confluence on 100×15 mm plastic dishes, and cells were harvested 24 hours later for measurement of GSH as outlined below. Also, to assess whether a nonspecific antioxidant effect of disulfiram or PDTC might account for cellular growth inhibition, we studied the effect of the potent lipophilic antioxidant probucol (1.0 to 1,000 µM) on proliferation of malignant cell lines. Finally, the generation of intracellular oxidants in response to disulfiram (0.625 to 5 µM), copper (0.2 to 1.6 µM $CuSO_4$) or 1.25 µM disulfiram plus various concentration of copper was measured directly, as outlined below.

To explore the role of cyclooxygenase inhibition in thiocarbamate toxicity, cells were cultured with or without disulfiram in the presence or absence of the COX1 and COX2 inhibitors indomethacin (5µg/ml) or sodium salicylate (1 mM). To probe whether disulfiram might be inducing growth retardation by interruption or stimulation of nitric oxide (NO) production, proliferation was studied with and without disulfiram in the presence and absence of the nitric oxide synthase inhibitor Nω-nitro-L-arginine added to growth medium (100 µM).

To further probe the role of copper in mediating cytotoxicity from disulfiram, cells were cultured with or without addition of the impermeate $Cu^{2+}$ chelator bathocuprioinedisulfonic acid (BCPS, 100 $\mu$M) added to medium to sequester $Cu^{2+}$ in the extracellular compartment. Cells were also treated 12 hours with various concentration of disulfiram (0.625 to 5.0 $\mu$M) and intracellular copper levels were measured as outlined below.

In additional experiments, cells were grown to confluence on 60×15 mm plastic Petri dishes and treated with 5 $\mu$M disulfiram or 5 $\mu$M disulfiram plus 1.6 $\mu$M $CuSO_4$ for 2 to 48 hours. Cells were lysed and levels of the pro-apoptotic protein p53, the anti-apoptotic protein Bcl-2, the cyclin inhibitor p21$^{WAF1/Cip1}$, and the cyclins A and B1 were measured by immunoblot assay as described below.

Finally, to study the effect of disulfiram on activation of select genes important for cellular proliferation, cells were grown to confluence on 100×15 mm plastic Petri dishes and treated with 5 $\mu$M disulfiram or 5 $\mu$M disulfiram plus 1.6 $\mu$M $CuSO_4$. Nuclear protein was harvested and electrophoretic mobility gel shift assays were performed for using DNA consensus binding sequence for the cyclic-AMP responsive element (CRE) as outlined below. To determine whether disulfiram and metals might directly influence transcription factor binding, in some experiments, 5 $\mu$M disulfiram and/or $CuSO_4$ 1.6 $\mu$M $CuSO_4$ (final concentrations) were added to the binding reaction of nuclear protein obtained from control cells stimulated with 10% FBS alone in the absence of drugs or metals. In vitro addition of disulfiram and $CuSO_4$ to the binding reaction was performed using either 2.5 mM dithiothreitol (DTT) or 3.0 mM GSH as a reducing agent in the binding buffer.

Measurement of Cytotoxicity and Apoptosis. To assess for cytotoxicity, cells were plated at a density of 50,000 per well on 24 well plates and grown for 24 hours. Disulfiram was then added. After an additional 36 hr, medium was removed and replaced with DPBS containing 0.1% trypan blue. Cell death was assessed by counting the average number of trypan blue positive cells per 10× field in 5 random fields for 4 separate wells. To determine whether disulfiram induced apoptosis, cells grown to confluence on 35 mm Petri dishes or on glass slides were treated with disufiram or DMSO as vehicle. Apoptosis was studied by terminal deoxynucleotidyl transferase (TdT) dependent 3'-OH fluorescein end-labeling of DNA fragments, using a Fluorescein-FragEL™ DNA fragmentation detection kit (Oncogene Research Products, Cambridge, Mass.). Apoptosis was also studied by visually assessing endonuclease dependent DNA fragmentation on ethidium bromide-stained agarose gels, as previously reported. See Dashtaki, et al. *J. Pharmacol. Exper. Ther*. 285:876–219 (1998).

DNA Cell Cycle Measurements. To study the effect of disulfiram on the DNA cell cycle, cells were grown to confluence in 25 cm² plastic flasks and treated for with 10% FBS plus DMSO vehicle, FBS and DMSO vehicle plus 1.6 $\mu$M $CuSO_4$, FBS plus 5 $\mu$M disulfiram or FBS plus 5 $\mu$M disulfiram and 1.6 $\mu$M $CuSO_4$. After 24 hr cells were trypsinized, washed twice in cold DPBS with 1 mM EDTA and 1% BSA, fixed 30 min in ice-cold 70% ethanol, and stained by incubation for 30 min at 37° C. in a 10 $\mu$g/ml solution of propidium idodide in DPBS and 1 mg/ml RNase A. DNA cell cycle measurements were made using a FACStar$^{PLUS}$ Flow Cytometer (Becton-Dickenson, San Jose, Calif.).

Measurement of Intracellular Copper. Cells were cultured in 12-well plastic tissue culture plates at an initial plating density of 50,000 cells/well, grown to confluence and treated with disulfiram or vehicle DMSO as outlined above. Media was removed and cells were washed twice with DPBS. Cells were then scraped into 1.0 ml of 3N HCl/10.0% trichloroacetic acid and hydrolyzed at 70° C. for 16 hr. The hydrolysate was centrifuged at 600 g for 10 min to remove debris and copper was measured in the supernatant using inductively coupled plasma emission spectroscopy (Model P30, Perkin Elmer, Norwalk, Conn.) at wavelengths of 325.754 and 224.700 nm. To minimize metal contamination, plasticware rather than glassware was used in these experiments, and double-distilled, deionized water was used for all aqueous media. Results are reported as ng copper/ml of hydrolysate.

Measurement of Intracellular Generation of Reactive Oxygen Species. Generation of reactive oxygen species in response to disulfiram with or without $CuSO_4$ was studied using 2',7'-dichlorofluorescin diacetate (DCF-DA, Molecular Probes, Eugene, Oreg.) and a modification of methods previously reported. See Royall, et al., *Archiv. Biochem. Biophys*. 302:348–355 (1993).

This method is based upon oxidation of dichlorofluorescin to 2',7'-dichlorofluorescein by $H_2O_2$ in the presence of cellular peroxidases. Cells were plated in 24 well plastic plates at 50,000 cells per well and grown to confluence. Media was aspirated from wells and replaced with 100 $\mu$l medium containing 10 $\mu$M DCF-DA, and plates were incubated at 370° C. for 30 min. The DCF-DA containing media was aspirated, cells were washed twice with media alone and 100 $\mu$l fresh media was added to wells. With the plate on the fluorescence micro-plate reader (HTS 7000) cells were stimulated with 25 $\mu$l of media containing 5× concentrations of disulfiram and/or $CuSO_4$ to provide final concentrations of 0–5.0 $\mu$M disulfiram and/or 0–1.6 $\mu$M $CuSO_4$, respectively. The relative concentration of dichlorofluroescein was measured immediately by monitoring fluorescence at 37° C. using an excitation wavelength of 485 nm and emission wavelength of 535 nm.

Measurement of Intracellular Glutathione. Disulfiram (5 $\mu$M), with or without 1.6 $\mu$M $CuSO_4$, was added to cells grown to confluence on 100×15 mm plastic dishes, and cells were harvested 24 hr later for measurement of GSH using the 5,5'-dithiobis(2-nitrobenzoic acid)-glutathione reductase recycling assay. See Anderson, M. E. *Methods Enzymol*. 113:548–555 (1985).

Immunossay for Proteins. Cells were lysed and proteins were isolated and quantitated by immunoassay as previously detailed (7,10), using 2 $\mu$g/ml of primary rabbit polyclonal antibodies against human Bcl-2 ($\Delta$C21), p53 (FL-393), p21$^{WAF1/Cip1}$ (H-164), cyclin A and cyclin B1 from Santa Cruz Biotechnology (Santa Cruz, Calif.) and peroxidase-labeled donkey polyclonal anti-rabbit IgG from Amersham Pharmacia Biotech (Buckinghamshire, England). Cells were placed on ice, washed twice with cold DPBS, scraped into 0.5 ml boiling buffer (10% [vol/vol] glycerol and 2% [wt/vol] sodium dodecyl sulfate [SDS] in 83 mM Tris, pH 6.8) and sheared by four passages through a pipette. Aliquots were removed for protein determination, using the BCA protein assay (Pierce). After 10% $\beta$-mercaptoethanol and 0.05% bromophenol blue were added, lysates were boiled for 5 min and stored at −80° C. until immunoblotting was performed. Proteins in defrosted samples were separated by SDS-polyacrylamide gel electrophoresis on 12% polyacrylamide gels (15 $\mu$g protein/lane) and electrotransferred to 0.45 $\mu$m Hybond ECL nitrocellulose membranes (Amersham Life Sciences) using the wet transblot method in transfer buffer (0.025 M Tris, 0.192 M glycine, 2.6 mM SDS, and 20%[vol/vol] methanol; pH 8.8) at 100 volts for 1 hr. Blots were blocked overnight at 4° C. with blocking buffer (PBS with 0.1% Tween 20) containing 5% fat-free milk powder (Carnation, Glendale, Calif.). After rinsing 5 times for 5 min each in PBS containing 0.1% Tween 20, blots were incubated for 1 hr at room temperature with 2.0 µg/ml of primary antibody. After rinsing again as above, blots were incubated for 1 hr at room temperature with horseradish peroxidase(HRP)-conjugated secondary antibody diluted 1:5,000 in blocking buffer. Immunoblots were rinsed again as above and detected via an enhanced chemiluminescence method (ECL Western blotting detection system, Amersham Life Science, Buckinghamshire, England). Autoradiographic film (X-OMAT AR, Eastman Kodak, Rochester, N.Y.) was exposed to immunoblots for 10, 30, or 60 sec to obtain satisfactory images.

Electrophoretic Mobility Shift Assays (EMSAs). Nuclear protein was isolated and DNA binding reactions were performed as previously described in detail. See, Dashtaki, et al. *J. Pharmacol. Exper. Ther.* 285:876–219 (1998); Kennedy et al., *Am. J Respir. Cell Mol. Biol.* 19:366–378 (1998).

Monolayers were washed twice in cold DPBS and equilibrated 10 min on ice with 0.7 ml cold cytoplasmic extraction buffer, CEB (10 mM Tris, pH 7.9, 60 mM KCl, 1 mM EDTA, 1 mM DTT) with protease inhibitors, PI (1 mM Pefabloc, 50 µg/ml antipain, 1 µg/ml leupeptin, 1 µg/ml pepstatin, 40 µg/ml bestatin, 3 µg/ml E-64 and 100 µg/ml chymostatin). The detergent Nonidet P-40 (NP-40) was added to a final concentration of 0.1% and cells were dislodged with a cell scraper. Nuclei were pelleted by centrifugation and washed with CEB/PI. Nuclei were then incubated for 20 min on ice in nuclear extraction buffer, NEB (20 mM Tris, pH 8.0, 400 mM NaCl, 1.5 mM $MgCl_2$, 1.5 mM EDTA, 1 mM DTT and 25% glycerol) with PI, spun briefly to clear debris and stored at −80° C. until performance of electrophoretic mobility shift assays. EMSAs were performed using consensus oligonucleotides (5'-AGAGATTGCCTGACGTCAGAGAGCTAG-3' and 3'-TCTCTAACGGACTGCAGTCTCTCGATC-5') for the cyclic-AMP responsive element CRE (ProMega, Madison, Wis.), end-labeled by phosphorylation with $[\gamma^{32}P]$-ATP and T4 polynucleotide kinase. DNA-protein binding reactions were performed with 2 µg of nuclear protein (as determined by the Pierce method) and 30–80,000 cpm of $^{32}$P-end-labelled double-stranded DNA probe in 10 mM Tris-HCl, pH 7.5, 50 mM NaCl, 0.5 mM EDTA, 0.5 mM DTT (except where indicated), 1 mM $MgCl_2$, 50 µg/ml poly dI-dC, and 4% glycerol. All components of the binding reaction with the exception of labeled probe were combined and incubated at room temperature for 10 min before addition of labeled probe and incubation for an additional 20 min. Competition experiments were performed with 10× unlabeled wild-type oligonucleotide sequences for CRE or NF-κB (p50, 5'-AGTTGAGGGGACTTTCCCAGGC-3' and 3'-TCAACTCCCCTGAAAGGGTCCG-5'), added before labeled probe. Samples were electrophoresed on a 5% nondenaturing polyacrylamide gel in Tris-glycine-EDTA (TGE, 120 mM glycine and 1 mM EDTA in 25 mM Tris, pH 8.5) buffer. Gels were dried and analyzed by autoradiography at −80° C. using an image intensifier screen.

Synthesis of Disulfiram-Metal Chelates. Chelates of disulfiram and a number of metals were synthesized by vigorous mixing of 150 mg of disulfiram in chloroform (2.5 mg/ml) with 30 ml of a 5× molar excess of $CuSO_4$, $ZnCl_2$, $C_3H_5AgO_3$ (silver lactate) or $HAuCl_4 3H_2O$ in double glass distilled deionized water. The mixture was centrifuged at 1,000 g for 10 min and the upper aqueous phase was discarded. As the lower chloroform phase was evaporated, the resulting disulfiram-metal chelates precipitated.

Statistical Analysis. Data are expressed as mean values ±standard error. The minimum number of replicates for all measurements was four, unless indicated. Differences between multiple groups were compared using one-way analysis of variance. The post-hoc test used was the Newman-Keuls multiple comparison test. Two-tailed tests of significance were employed. Significance was assumed at $p<0.05$.

EXAMPLE 1

Disulfiram is Antiproliferative Against Malignant Human Cell Lines

M1619 human melanoma cell line was used to test the antiproliferative characteristics of disulfiram. Cells stimulated with 10% fetal bovine serum (FBS) were plated at a density of 50,000 cells per well. DMSO vehicle (5 µl per ml) or disulfiram (DS) at various concentrations was added to wells. After 48 hr, proliferation was quantitated by assessing the cell number-dependent reduction of the soluble yellow tetrazolium dye 3-[4,5-dimethylthiazol]-2yl-2,5-diphenyl tetrazolium bromide (MTT) to its insoluble formazan, measured as the absorbance at 540 µm ($A_{540}$). *$p<0.01$ compared to FBS+DMSO vehicle control. As shown in FIG. 1A, at concentrations readily achievable in humans on usual clinical doses (see, e.g., Faiman et al. *Clin. Pharmacol. Ther.* 36:520–526 (1984)), disulfiram was a potent inhibitor of growth in vitro for M1619 melanoma.

A variety of other malignant human cell lines including M1585 melanoma, prostatic adenocarcinoma, nonsmall cell, small cell lung cancer, and adenocarcinoma of the breast were tested by the same method as described above. Cells stimulated with 10% fetal bovine serum (FBS) were plated at a density of 50,000 cells per well. In some studies (treatment initially) DMSO vehicle (5 µl per ml) or disulfiram (DS) was added to wells at the indicated concentrations. After 48 hr, proliferation was quantitated as described above. In other studies (treatment after 24 hr) cells were grown for 24 (M1619, M1585 and H596 lung) or 48 hr (breast). DMSO vehicle (5 µl per ml) or disulfiram (DS) was added to wells at the indicated concentrations. After an additional 24 (lung) or 48 hours (breast), proliferation was quantitated as described above. Percent inhibition of growth was calculated as $100\times(1.0=A_{540}$ of MTT formazan in disulfiram treated cells/mean $A_{540}$ of MTT formazan in DMSO vehicle treated cells). In some cell lines, a modest (<10%) but statistically significant inhibitory effect was observed with DMSO vehicle alone. The results are summarized in Table 1. Each value represents a mean of at least 4 experiments. $^{A}p<0.01$ compared to FBS+DMSO vehicle control.

As shown in Table 1, disulfiram was effective in inhibiting the growth of many different malignant cells. This was true whether disulfiram was added to culture media when cells were plated or later, after cell had grown for 24–48 hours.

TABLE 1

DISULFIRAM IS ANTIPROLIFERATIVE FOR MALIGNANT CELLS

| | Mean Percent Inhibition of Growth Concentration of Disulfiram ($\mu$M) | | | |
|---|---|---|---|---|
| Cell Line | 0.625 | 1.25 | 2.5 | 5.0 |
| Treatment initially | | | | |
| Melanoma M1585 | $100 \pm 0^A$ | $100 \pm 0^A$ | $100 \pm 0^A$ | $100 \pm 0^A$ |
| Prostate carcinoma CRL 1435 (PC-3) | $6 \pm 6$ | $29 \pm 5^A$ | $48 \pm 2^A$ | $86 \pm 2^A$ |
| Squamous lung carcinoma NCI-H520 | $76 \pm 3^A$ | $82 \pm 4^A$ | $77 \pm 4^A$ | $78 \pm 3^A$ |
| Adenosquamous lung carcinoma NCI-H596 | $47 \pm 4^A$ | $57 \pm 4^A$ | $50 \pm 3^A$ | $50 \pm 4^A$ |
| Small cell lung carcinoma NCI-H82 | $68 \pm 3^A$ | $76 \pm 6^A$ | $76 \pm 5^A$ | $72 \pm 3^A$ |
| Breast carcinoma MDA-MB-453 | $69 \pm 4^A$ | $94 \pm 2^A$ | $100 \pm 0^A$ | $100 \pm 0^A$ |
| Treatment after 24 hr | | | | |
| Melanoma M1619 | $59 \pm 4^A$ | $35 \pm 4^A$ | $39 \pm 3^A$ | $37 \pm 4^A$ |
| Melanoma M1585 | $74 \pm 4^A$ | $49 \pm 7^A$ | $41 \pm 2^A$ | $37 \pm 6^A$ |
| Lung carcinoma NCI-H596 | $30 \pm 3^A$ | $30 \pm 3^A$ | $29 \pm 1^A$ | $34 \pm 3^A$ |
| Breast carcinoma MDA-MB-453 | $26 \pm 5^A$ | $26 \pm 2^A$ | $39 \pm 2^A$ | $46 \pm 4^A$ |

EXAMPLE 2

Antiproliferative Activity of Disulfiram Depends on Complexation with Copper

Figure 1B:
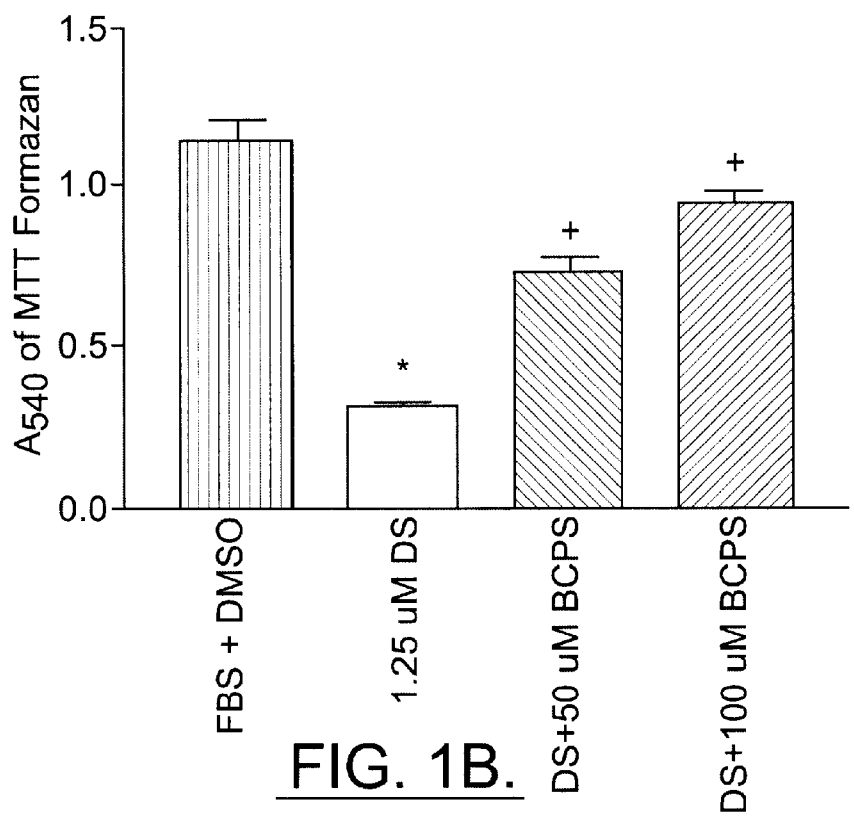
FIG. 1B demonstrates that the cell-impermeate $Cu^{2+}$ chelator bathocuproine-disulfonic acid prevents growth inhibition by disulfiram.

M1619 melanoma cells stimulated and plated as described in Example 1. 1.25 $\mu$M disulfiram (DS) or DMSO vehicle (5 $\mu$l per ml) was added to wells in the absence or presence of 50 or 100 $\mu$M bathocuproine-disulfonic acid (BPS). After 48 hours, proliferation was quantitated as described. *p<0.001 compared to FBS+DMSO; +p<0.001 compared to FBS+DS. As shown in FIG. 1B, the cell-impermeate $Cu^{2+}$ chelator bathocuproine-disulfonic acid prevents growth inhibition from disulfiram.

EXAMPLE 3

Copper Enhances the Antiproliferative Activity of Disulfiram.

Figure 1C:
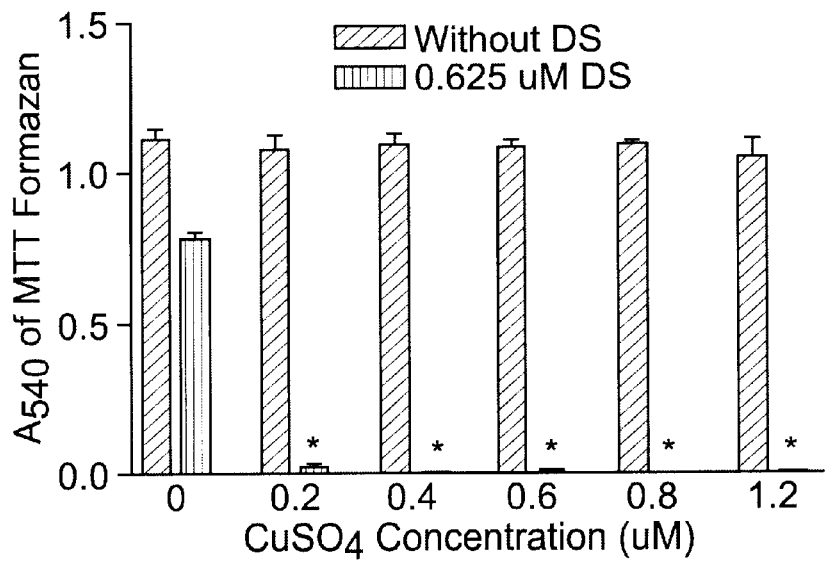
FIG. 1C is a schematic diagram demonstrating that supplementation of growth medium with copper enhances the antiproliferative activity of disulfiram.

M1619 melanoma cells plated and stimulated as described in Example 1 were grown for 24 hr and supplemented with $CuSO_4$ or $CuSO_4$ plus 0.625 PM disulfiram. After an additional 24 hr proliferation was quantitated. As shown in FIG. 1C, supplementation of growth medium with copper enhances the antiproliferative activity of disulfiram. The addition of even 0.2 PM $CuSO_4$ to medium converts 0.625 $\mu$M disulfiram from a 50% inhibitory ($IC_{50}$) concentration into a 100% inhibitory ($IC_{100}$) concentration of drug. *p<0.001 compared to no $CuSO_4$.

Figure 1D:
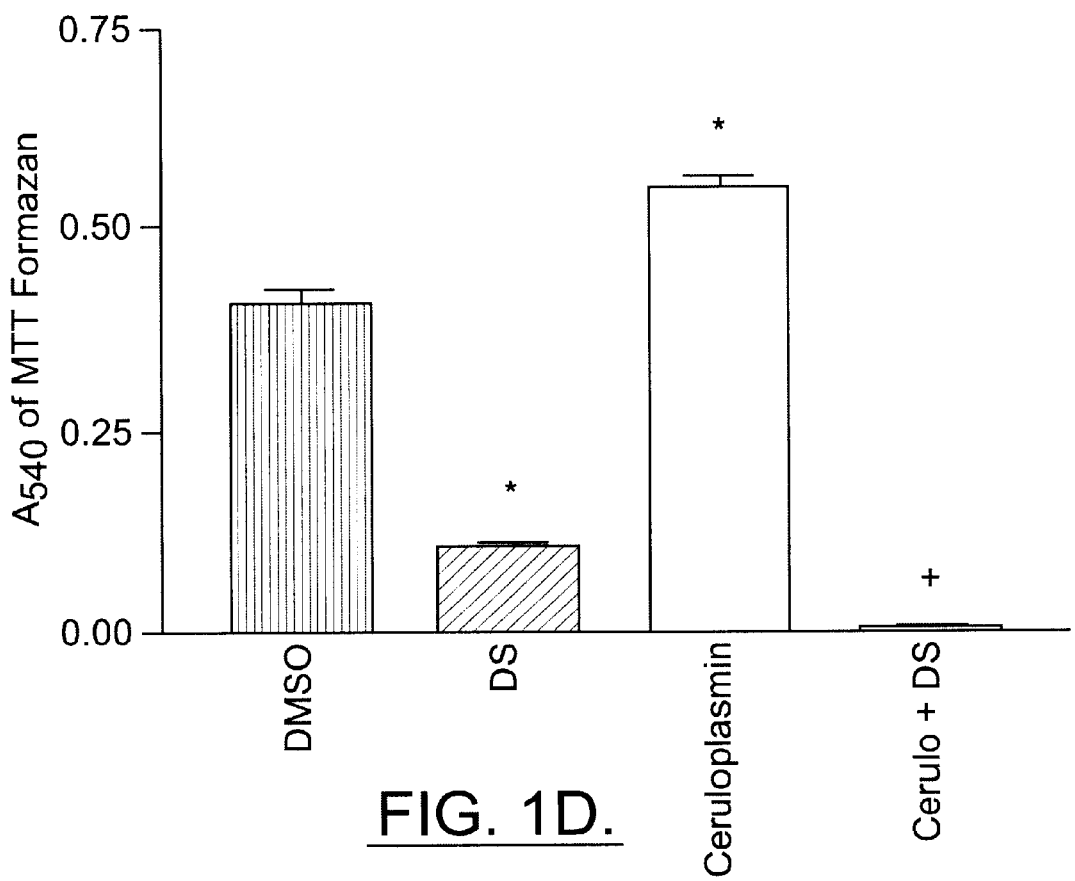
FIG. 1D shows that ceruloplasmin can serve as a source of copper for enhancing the antiproliferative activity of disulfiram.

M1619 melanoma cells were plated, stimulated and grown for 24 hr in the presence or absence of 0.625 $\mu$M disulfiram or 5 $\mu$l/ml DMSO vehicle in the presence or absence of human ceruloplasmin (Cerulo) at a concentration representing the upper level in normal human serum (500 $\mu$g/ml). After 24 hours, proliferation was quantitated. *p<0.001 compared to FBS+DMSO; +p<0.001 compared to FBS+DS. As shown in FIG. 1D, ceruloplasmin can serve as a source of copper for enhancing the antiproliferative activity of disulfiram.

EXAMPLE 4

Disulfiram Induces Apoptosis

Figure 2A:
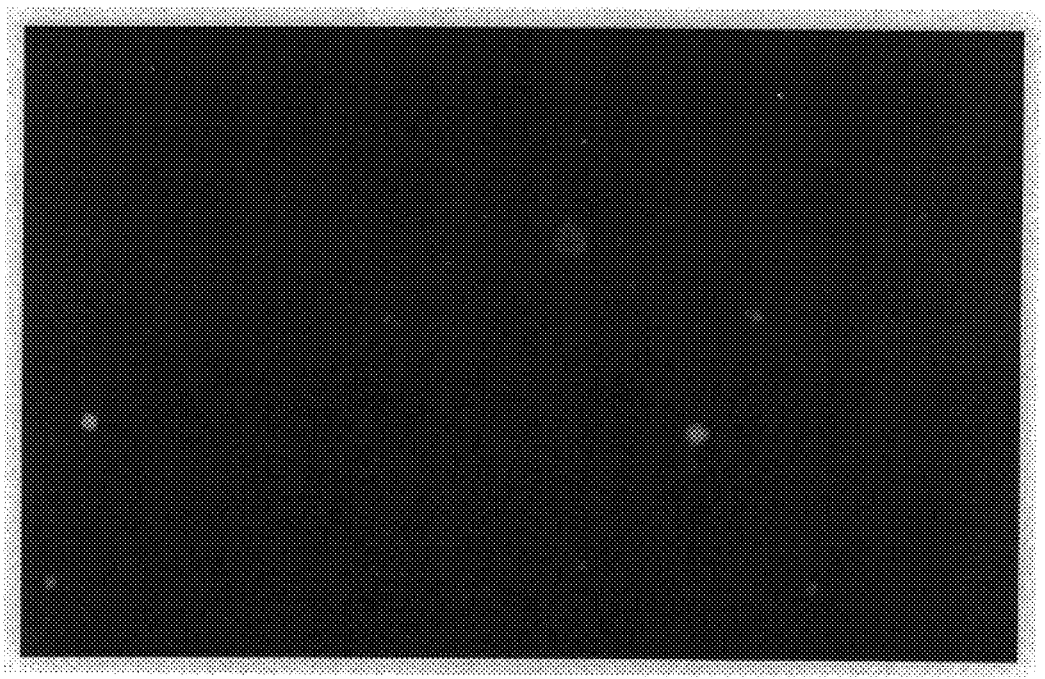
FIG. 2A shows the result of a control experiment, in which M1619 melanoma cells were treated with DMSO vehicle.
Figure 2B:
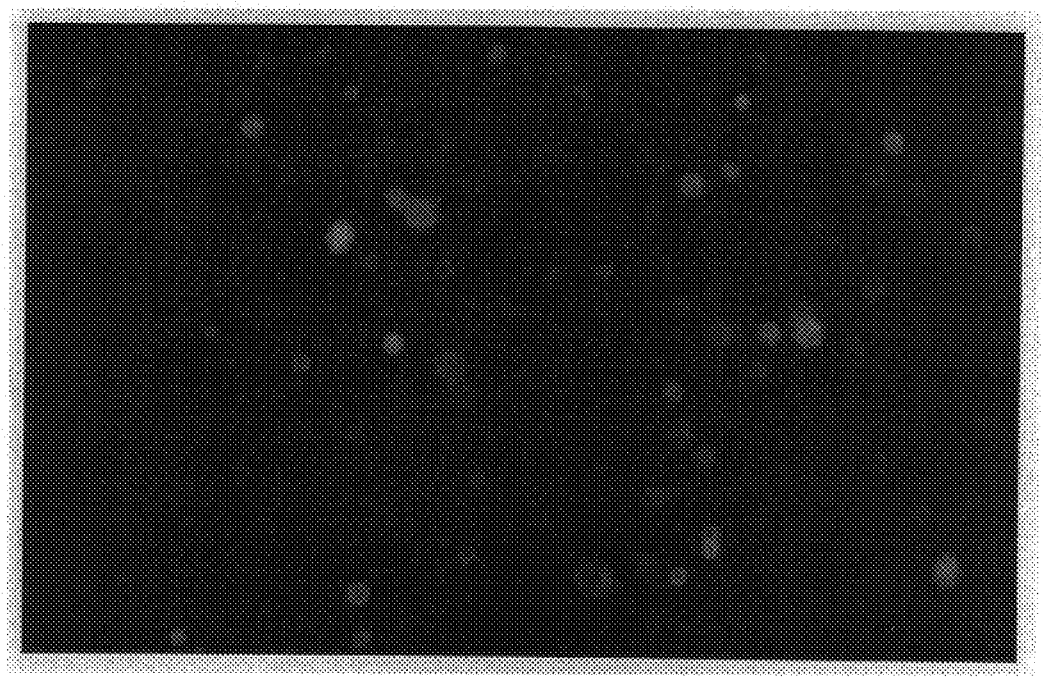
FIG. 2B demonstrates that apoptosis was induced in M1619 melanoma cells treated with 5 μM disulfiram.

M1619 melanoma cells were grown to confluence on 35 mm Petri dishes or on glass slides and treated for 15 hours with disufiram or DMSO as vehicle. Apoptosis was studied by terminal deoxynucleotidyl transferase (TdT) dependent 3'-OH fluorescein end-labeling of DNA fragments, using a Fluorescein-FragEL™ DNA fragmentation detection kit (Oncogene Research Products, Cambridge, Mass.). As shown in FIG. 2A and 2B, apoptosis was induced in M1619 melanoma cells treated with 5 $\mu$M disulfiram. Disulfiram markedly increases 3'-OH fluorescein end-labeling of DNA fragments. Treatment of monolayers with even low doses of disulfiram markedly increased trypan blue dye uptake. 6±2, 8±3.6 and 94±18 trypan blue positive cells per well, respectively were observed for untreated, DMSO vehicle treated or H520 lung adenosquamous carcinoma cells treated with 0.625 $\mu$M disulfiram. 12±0.9, 16.5±2.1 and 93±12 trypan blue positive cells per well, respectively, were observed for untreated, DMSO-treated or H82 small lung cancer cells treated with 0.625 $\mu$M disulfiram. p<0.001 compared to untreated or DMSO vehicle treated controls. In addition, disulfiram also increased DNA laddering on ethidium bromide-stained agarose gels (data not shown).

EXAMPLE 5

Disulfiram and Cooper Induce $G_2$ Cell Cycle Arrest and Apoptosis

Figure 3A:
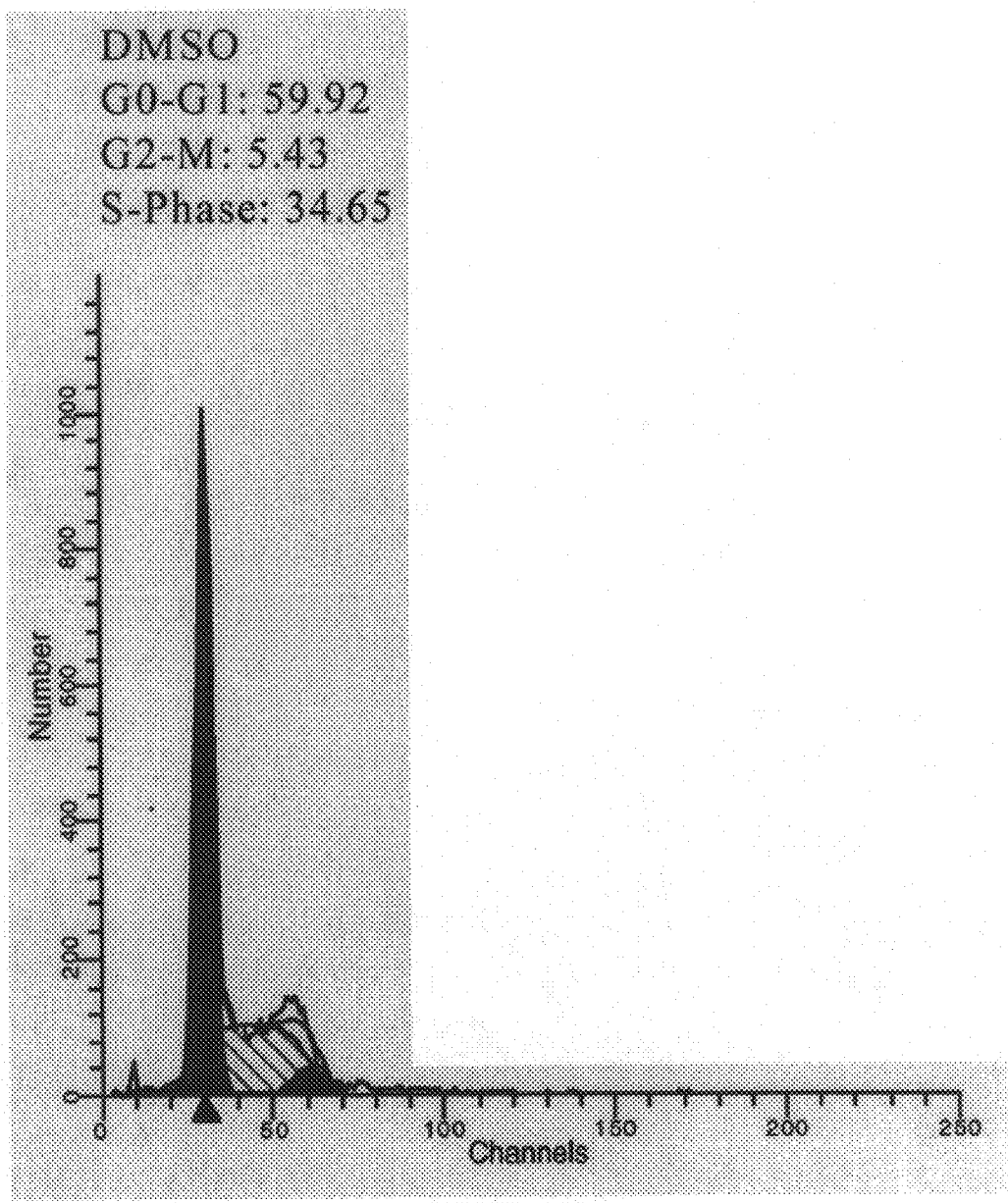
FIG. 3A is shows the flow cytometric analysis of the growth of unsynchronized M1619 melanoma cells in the presence of DMSO vehicle.
Figure 3B:
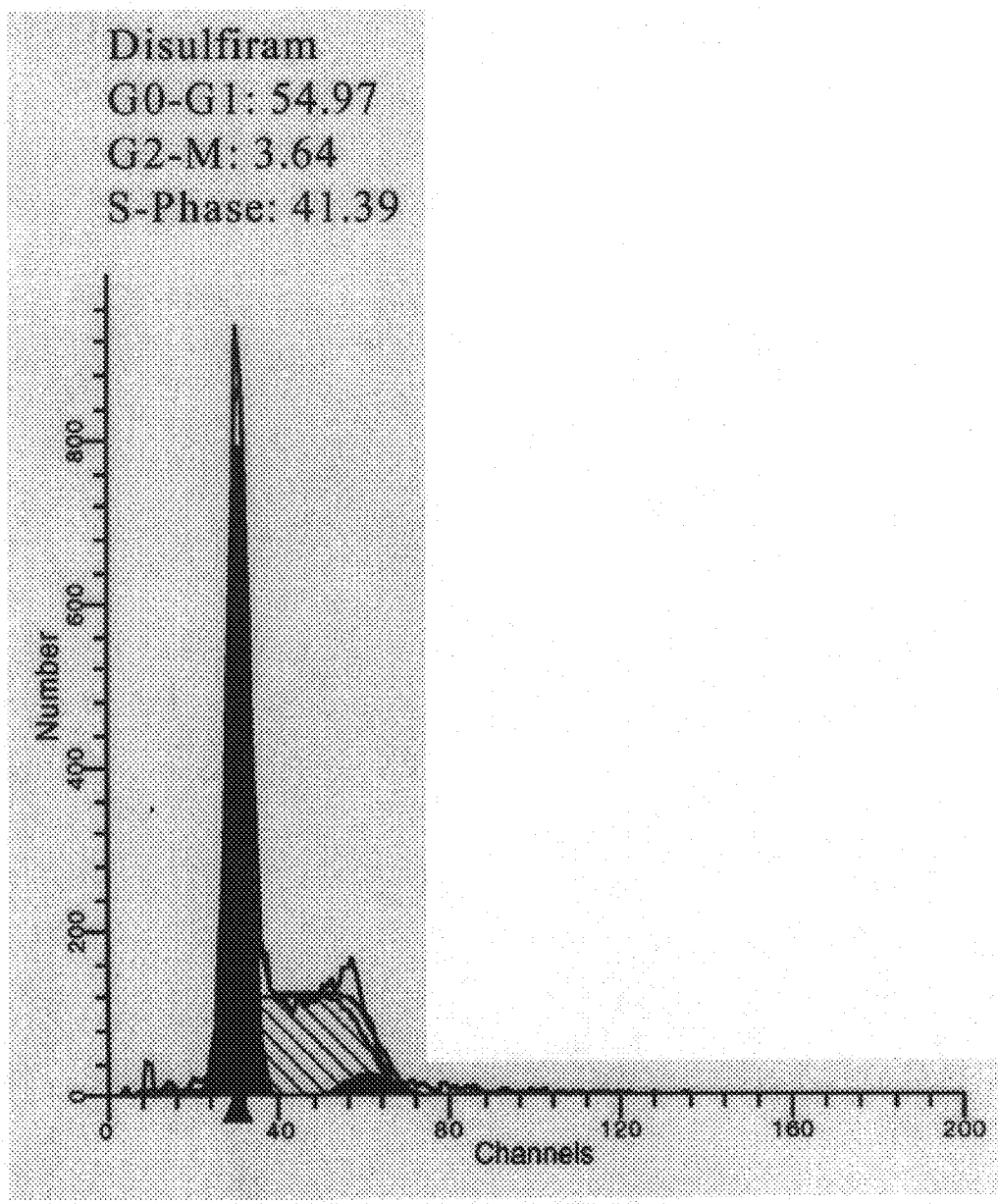
FIG. 3B is flow cytometric analysis of cells treated with 5 μM disulfiram, which shows that disulfiram reduces the number of cells in $G_0$–$G_1$ and increases the portion in S phase of the cell cycle in M1619 melanoma cells.
Figure 3C:
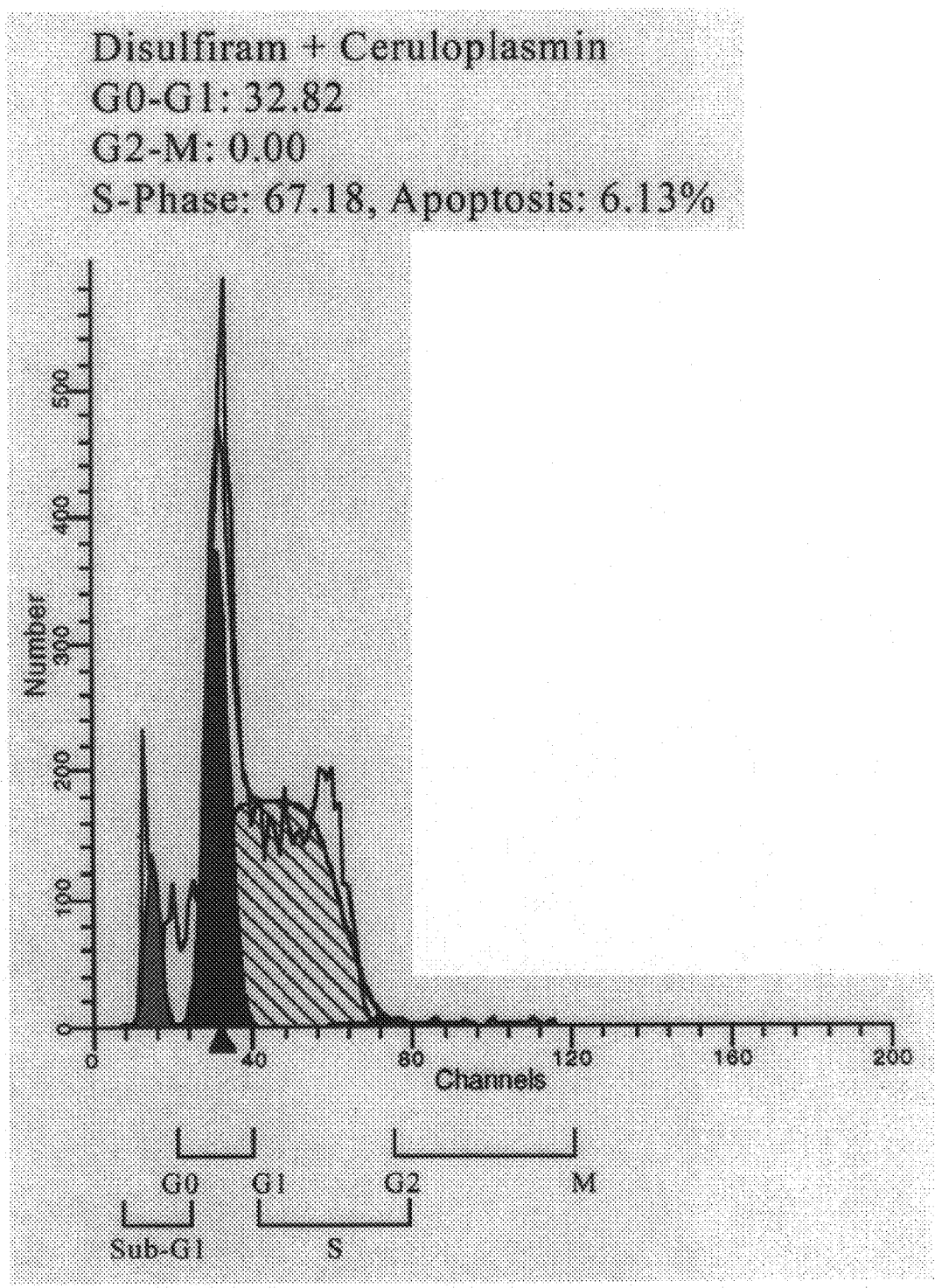
FIG. 3C is flow cytometric analysis of cells treated with 5 μM disulfiram plus 250 μg/ml ceruloplasmin (Cerulo) which induce $G_2$ cell cycle arrest and apopotosis in M1619 melanoma cells.

Unsynchronized M1619 melanoma cells were incubated with DMSO (FIG. 3A), 5 $\mu$M disulfiram (FIG. 3B), or 5 $\mu$M disulfiram plus 250 $\mu$g/ml of ceruloplasmin (FIG. 3C). Twenty-four hours later, cells were harvested and flow cytometric analysis was performed. The proportion of nuclei in each phase of the cell cycle (brackets) was determined with MODFIT DNA analysis software. Disulfiram increases the portion of cells in S phase. The combination of disulfiram and ceruloplasmin further increases the number of cells in S phase, induces $G_2$ cell cycle arrest and apoptosis. FIG. 3A shows the growth of unsynchronized M1619 melanoma cells in the presence of DMSO vehicle. FIG. 3B shows that 5 $\mu$M disulfiram induces the number of cells in $G_0$–$G_1$ and increases the portion in S phase of the cell cycle in M1619 melanoma cells. FIG. 3C shows that 5 $\mu$M disulfiram plus 250 $\mu$g/ml ceruloplasmin (Cerulo) induces G2 cell cycle arrest and apopotosis in M1619 melanoma cells.

EXAMPLE 6

Disulfiram does not Decrease Proliferation through Redox Mechanisms

M1619 melanoma cells stimulated with 10% FBS were plated at a density of 50,000 cells per well, grown for 24 hours, and treated with 5 $\mu$M disulfiram or 5 $\mu$l/ml DMSO vehicle, in the presence or absence of the nitric oxide synthase inhibitor $N_\omega$-nitro-L-arginine (LNAME, 100 $\mu$M). After an additional 24 hours, proliferation was quantitated as described in Example 1. *p<0.01 compared to DMSO; +p<0.001 compared to DMSO.

Figure 4:
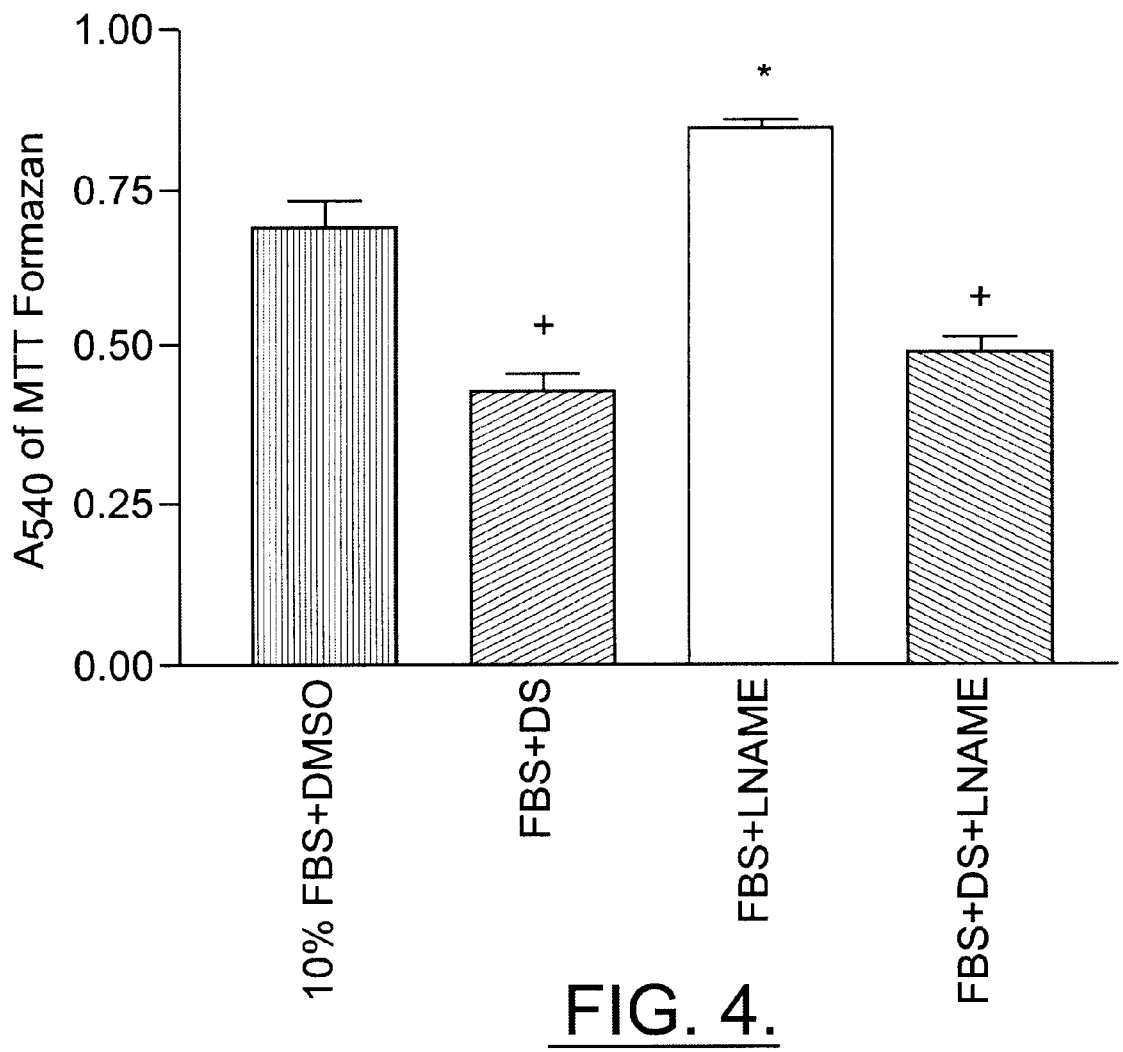
FIG. 4 demonstrates that antiproliferative activity of disulfiram is not mediated by nitric oxide.

FIG. 4 demonstrates that antiproliferative activity of disulfiram is not mediated by nitric oxide. While the nitric oxide synthase inhibitor $N_\omega$-nitro-L-arginine (LNAME) alone slightly enhanced cellular growth, LNAME did not reduce the antiproliferative effect of disulfiram. Thus, disulfiram does not appear to inhibit growth by adversely affecting cellular redox state.

In addition, reactive oxygen species were measured in M1619 cells treated with disulfiram, copper, or both, using the $H_2O_2$-sensitive intracellular probe 2',7'-dichloroflurorescin, as disclosed in Royall et al., *Archiv. Biochem. Biophys.* 302:348–355 (1993).

Neither disulfiram (0.625 to 5 μM), CUSO$_4$ (0.2–1.6 μM) nor the combination of 1.25 μM disulfiram and 0.2 to 1.6 μM CUSO$_4$ caused measurable generation of reactive oxygen species in M1619 cells. The baseline fluorescence of 1,431±23 units was not increased by any of the treatments. Likewise, disulfiram failed to deplete GSH in M1619 cells (228±18 for FBS alone; 254±7 for DMSO vehicle control; 273±11 μM GSH/μg cell protein for 5 μM disulfiram), and the combination of 5.0 μM disulfiram and 1.6 μM CuSO$_4$ even increased intracellular GSH (293±16 μM GSH/μg cell protein; p<0.05 compared to FBS alone). In addition, the potent antioxidant probucol did not significantly inhibit growth of any of our tumor cell lines.

EXAMPLE 7

Figure 5A:
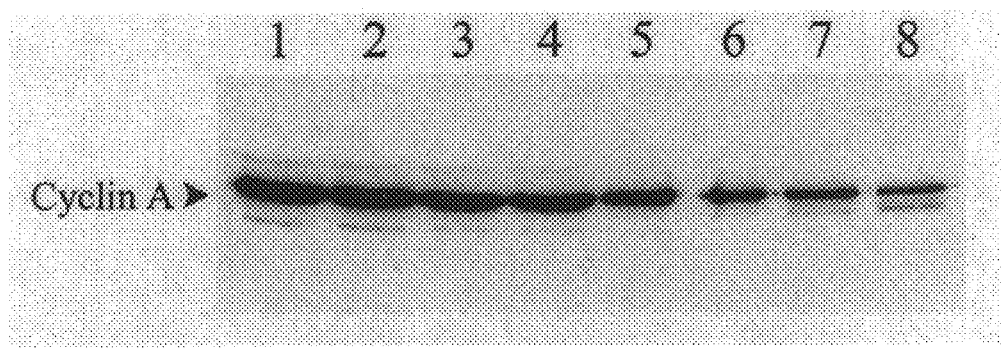
FIG. 5A is a photograph of Western blot analysis of cyclin A expression in M1619 cells treated with DMSO or disulfiram.

Disulfiram Plus Copper Reduce Expression of the Cell-cycle Protein Cyclin A and Inhibit DNA Binding of Transcription Factors to DNA Regulatory Elements Important for Cyclin A Expression M1619 melanoma cells were plated at equal densities in 60×15 mm plastic dishes, grown to 80% confluence and treated with DMSO vehicle (5 μl/ml), disulfiram (5 μM), or the combination of disulfiram and CuSO$_4$ (1.6 μM). After the indicated times, cells were lysed and protein extracts were subjected to SDS-polyacrylamide gel electrophoresis (PAGE) followed by Western blotting using a rabbit polyclonal antibody. Typical experiments are shown for 2, 4, 8, 12, 24 and 48 hours of treatment. FIG. 5A shows that disulfiram plus copper reduce expression of the cell-cycle protein cyclin A, providing a potential proximate explanation for the antiproliferative effects of this drug-metal combination. In contrast, levels of cyclin B1 remained unchanged, and, in the cell lines we studied, disulfiram had no consistent effect on expression of the cell cycle inhibitor p21$^{WAF1/CIP1}$ (data not shown).

Figure 5B:
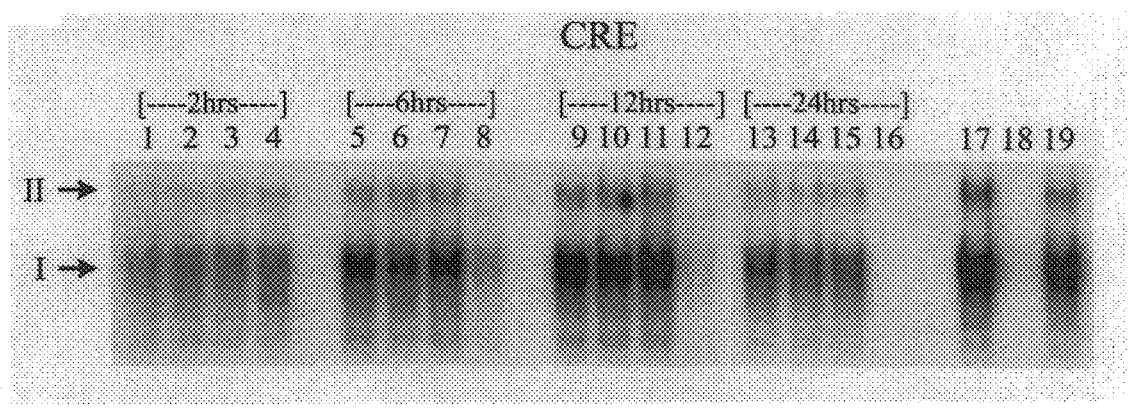
FIG. 5B is a photograph of a gel shift assay showing that disulfiram and copper inhibit transcription factor binding to the cyclic-AMP responsive element (CRE).

Cyclin A expression is regulated in part by binding of c-Fos and CREB-1 protein heterodimers to a cyclic-μMP responsive element (CRE) in the cylin A promoter. See Sylvester et al., J. Clin. Invest. 101:940–948 (1998). M1619 melanoma cells were grown to 80% confluence on 100×15 mm plastic Petri dishes, treated, nuclear protein was harvested and electrophoretic mobility gel shift assays were performed. CRE complexes (I and II) are labeled. Treatment of cells for 6, 12 or 24 hours with the combination of 5 μM disulfiram and 1.6 μM cupric sulfate substantially interrupts transcription factor binding to CRE. FIG. 5B shows that the combination of disulfiram and copper essentially eliminates transcription factor binding to CRE after 6 hours of treatment, an expected result of which would be reduced transcription of the cyclin A gene. EMSAs for 2, 6, 12 or 24 hours of treatment: fetal bovine serum (FBS) alone, lanes 1, 5, 9, and 13; FBS+DMSO vehicle, lanes 2, 6, 10,14; FBS+disulfiram, lanes 3, 7, 11,15; FBS+disulfiram+CuSO$_4$, lanes 4, 8,12,16. Competition experiments are shown in lanes 17–19: Lane 17, FBS alone; lane 18, FBS with 10× unlabeled CRE probe added to binding reaction; lane 19, FBS with 10× unlabeled NF-κB probe added to binding reaction.

Figure 5C:
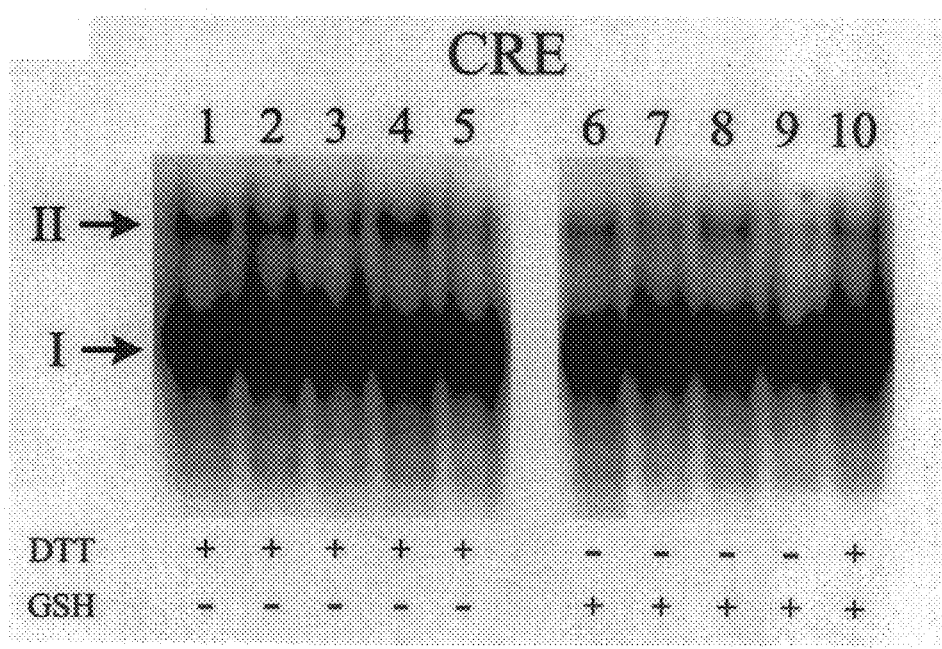
FIG. 5C is a photograph of a gel shift assay in which disulfiram or disulfiram plus copper was directly added to the binding reaction.

Addition of disulfiram and copper directly to the binding reaction also reduced DNA binding to CRE (FIG. 5C, lane 5). This reduction was even more pronounced when the binding reaction was performed with GSH instead of DTT as the reducing agent (FIG. 5C, lane 9), and inhibition of CRE binding by disulfiram and copper in the presence of GSH was partially reversed by simultaneous addition of DTT (FIG. 5C, lane 10). Electrophoretic mobility shift assays (EMSAs) were conducted in the same methods as described. The results are shown in FIG. 5C. In Lane 1, fetal bovine serum (FBS) alone; lane 2, FBS+DMSO vehicle; lane 3, FBS+disulfiram (5 μM); lane 4, FBS+1.6 μM CuSO$_4$; lane 5, FBS+disulfiram+CuSO$_4$; lane 6, FBS alone; lane 7, FBS+disulfiram; lane 8, FBS+CuSO$_4$; lane 9, FBS+disulfiram+CuSO$_4$; lane 10, FBS+disulfiram+CuSO$_4$. In lanes 1–5, DTT (2.5 mM) was added to the binding reaction as a reducing agent, whereas in lane 6–9, GSH (3.0 mM) was used. Disulfiram and copper reduced transcription factor binding to CRE, but the effect was more pronounced when the binding reaction was performed with GSH (lane 9) instead of DTT (lane 5) as a reducing agent. Inhibition of binding to CRE by disulfiram and copper in the presence GSH was partially reversed by simultaneous addition of DTT.

EXAMPLE 8

Metals Other than Copper can Enhance the Antiproliferative Activity of Disulfiram The absorption of copper at both the intestinal and cellular level is blocked by zinc cations, leading to the use of zinc acetate as the preferred treatment for Wilson's disease, the inherited disorder of copper overload. See Brewer, et al., J. Am. Coll. Nutr. 9:487–491 (1990); Reeves, et al., J. Nutr. 126:1701–1712 (1996). We therefore determined whether zinc supplementation of medium could inhibit the antiproliferative activity of disulfiram, which appears to be copper-dependent.

Figure 6A:
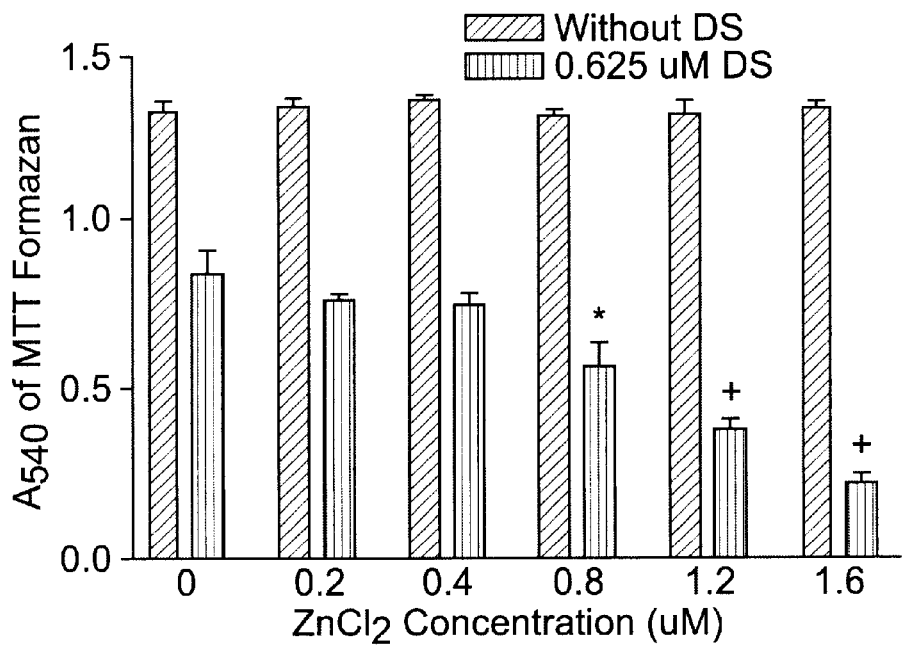
FIG. 6A demonstrates that zinc potentiates the antiproliferative activity of disulfiram.

M1619 cells were stimulated and plated as in Example 1. After 24 hours cells were treated with indicated concentrations of zinc chloride (ZnCl$_2$) in the absence or presence of 0.625 μM disulfiram. After an additional 24 hours, cell number was quantitated. The results are shown in FIG. 6A. *p<0.01 compared to no ZnCl$_2$;+p<0.001 compared to no ZnCl$_2$. Surprisingly, zinc chloride also substantially enhanced the antiproliferative potential of disulfiram.

Figure 6B:
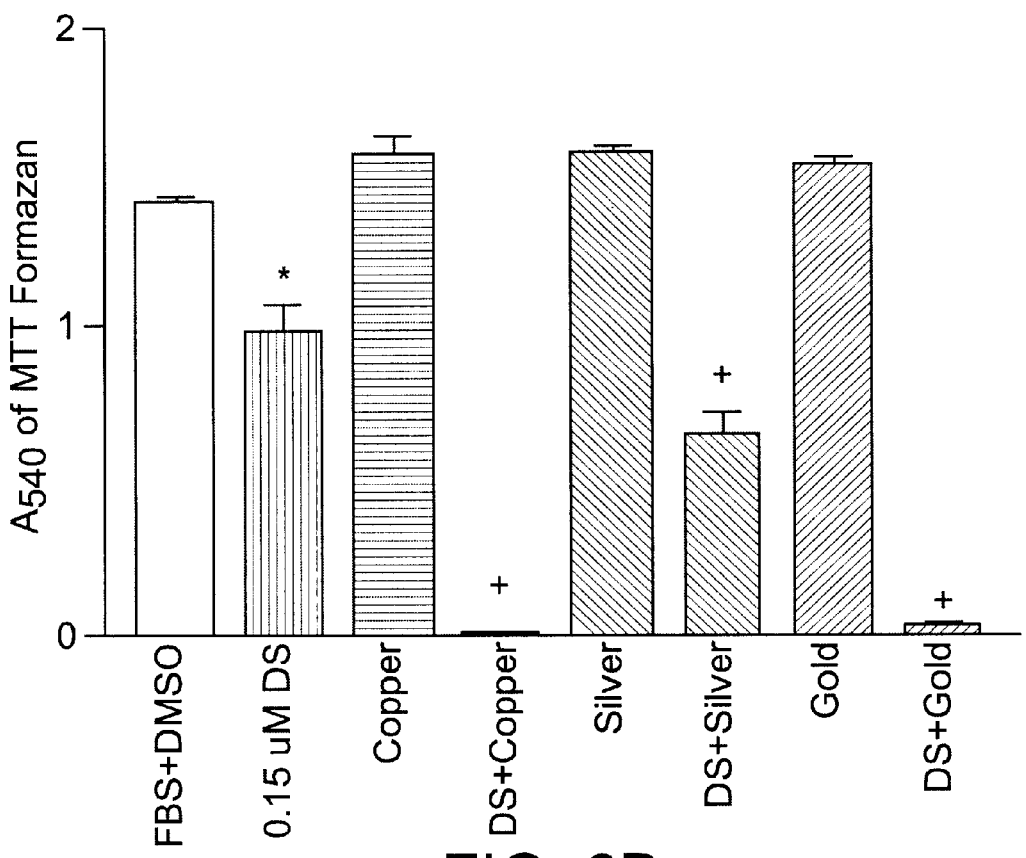
FIG. 6B demonstrates that the antiproliferative activity of disulfiram is enhanced by supplementation of medium with other heavy metals.

M1619 cells plated and stimulated as above were treated with FBS alone, DMSO vehicle (5 μl/ml), disulfiram (DS, 0.15 μM), 5 μM concentrations of metal salts (cupric sulfate, CuSO$_4$; silver lactate, C$_3$H$_5$AgO$_3$; gold chloride, HAuCl$_4$3H$_2$O,) or the combination of DS plus metal salts. After 48 hr cell number was quantitated. *p<0.05 compared to DMSO;+p<0.001 compared to DS alone. FIG. 6B shows that not only copper and zinc, but also salts of gold and silver can synergistically enhance the antiproliferative activity of disulfiram.

Figure 6C:
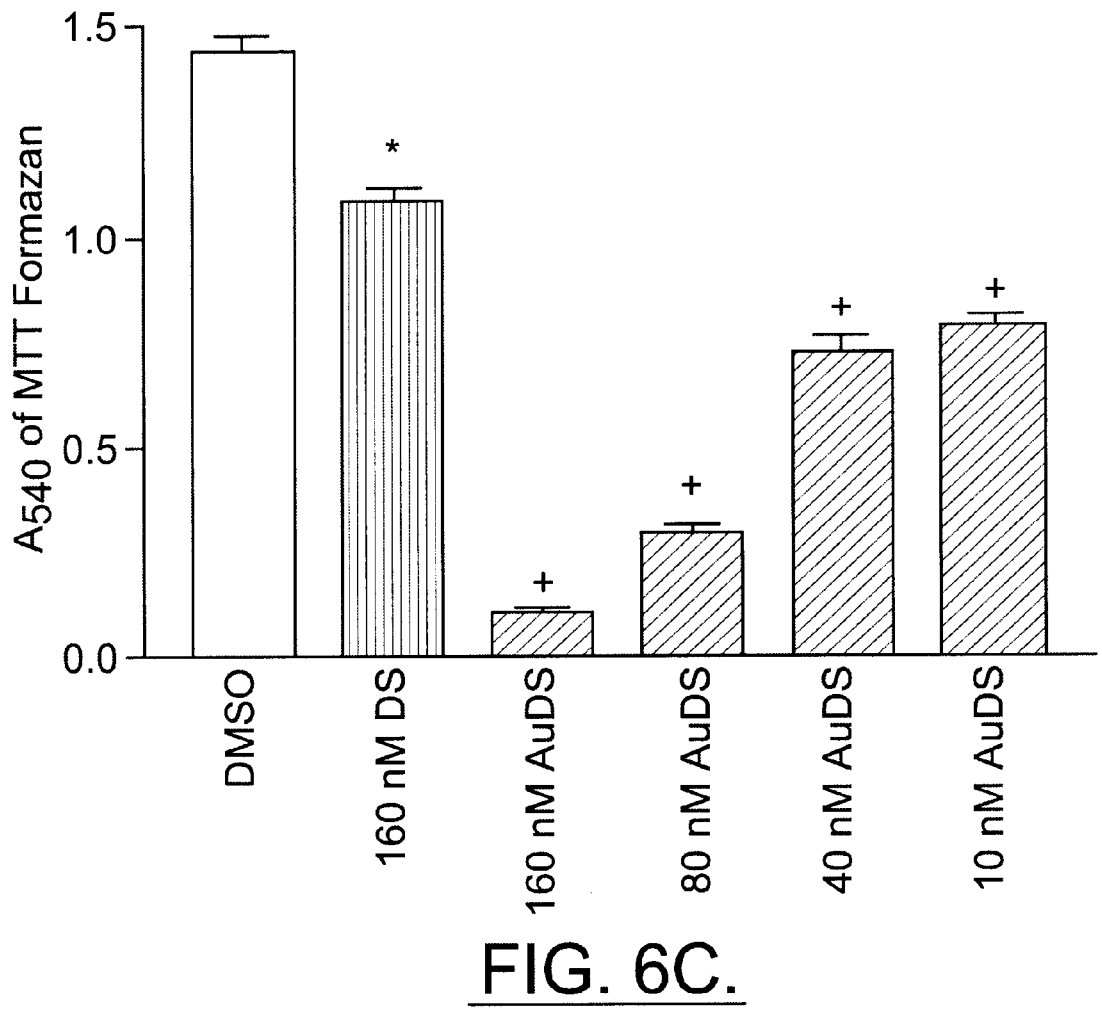
FIG. 6C demonstrates that complexes of disulfiram with gold exhibit enhanced antiproliferative activity.

In light of these findings, we synthesized chelates of disulfiram with a number of metal ions, including Cu$^{2+}$, Zn$^{2+}$, Ag$^{1+}$, or Au$^{3+}$. During generation of disulfiram-metal complexes, chelation of metal ions from the aqueous phase was suggested by a color change in the disulfiram-containing chloroform phase (from pale yellow to brilliant golden orange with complexation of gold ions). M1619 cells plated and stimulated as above were treated with FBS alone, DMSO vehicle (5 μl/ml), disulfiram (DS, 160 nM) or concentrations of gold disulfiram (AuDS) as indicated. After 48 hr cell number was quantitated. *p<0.001 compared to DMSO; +p<0.001 compared to DS. FIG. 6C demonstrates that complexes of disulfiram with gold exhibit enhanced antiproliferative activity. All metal complexes showed increased antiproliferative activity compared to disulfiram, but the most active compound was formed by the complex of gold with disulfiram (FIG. 6C), which was antiproliferative at nM concentrations.

EXAMPLE 9

Disulfiram Potentiates the Antineoplastic Effect of Ciplatin and Carmustine

M1619 melanoma cells were cultured in 10% FBS and RPMI 1640 at a density of 50,000 cells/well in 24 well plates. After 48 hours cisplatin and 2.5 $\mu$M disulfiram or DMSO (5 $\mu$l per ml) were added to medium. After an additional 24 hours, proliferation was quantitated. Each bar represents mean MTT formazan absorbance in a minimum of 4 experiments.

M1619 cells were cultured as above with addition of carmustine and 0.6 $\mu$M disulfiram or DMSO (5 $\mu$l per ml) to medium. After 24 hours, proliferation was quantitated.

Table 2 shows that the combination of disulfiram and cisplatin or disulfiram and carmustine is significantly more antiproliferative against M1619 cells than cisplatin or carmustine alone. Each number represents mean MTT formazan absorbance in a minimum of 4 experiments. $^A$p<0.05 compared to DMSO vehicle; $^B$p<0.01 compared to DMSO vehicle; $^C$p<0.001 compared to DMSO vehicle.

Disulfiram was more potent as a growth inhibitor of neoplastic cell lines than its sulfhydryl-containing relative PDTC. As an example, the 50% inhibitor concentration (IC$_{50}$) against M1585 melanoma cells was approximately 1.25 $\mu$M for PDTC but was only 0.3 $\mu$M for disulfiram. This suggests that the active antiproliferative construct of thiocarbamates might be the oxidized dimeric disulfide rather than the reduced thiol-containing monomeric form employed frequently as an antioxidant.

TABLE 2

DISULFIRAM POTENTIATES
THE ANTIPROLIFERATIVE ACTIVITY OF CHEMOTHERAPEUTIC
AGENTS

| | A540 of MTT Formazan | |
|---|---|---|
| | DMSO vehicle | |
| A. Cisplatin (ng/ml) | | Disulfiram 2.5 $\mu$M |
| 0 | 1.433 ± 0.038 | |
| 1 | 1.739 ± 0.041 | 1.369 ± 0.033$^B$ |
| 10 | 1.447 ± 0.047 | 1.221 ± 0.028 |
| 100 | 1.372 ± 0.052 | 1.183 ± 0.038$^A$ |
| 1,000 | 1.381 ± 0.098 | 0.921 ± 0.027$^A$ |
| B. Carmustine ($\mu$M) | | Disulfiram 0.6 $\mu$M |
| 0 | 0.104 ± 0.010 | |
| 1 | 0.197 ± 0.004 | 0.042 ± 0.003$^C$ |
| 10 | 0.152 ± 0.011 | 0.025 ± 0.002$^C$ |
| 100 | 0.020 ± 0.002 | 0.030 ± 0.023 |
| 1,000 | 0.003 ± 0.000 | 0.004 ± 0.000 |

Many modifications and other embodiments of the invention will come to mind to one skilled in the art to which this invention pertains, having the benefit of the teachings presented in the descriptions and the associated drawings contained herein. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

REFERENCES

1. Chinery, R., Brockman, J. A., Peeler, M. O., Shyr, Y., Beauchamp, R. D, and Coffey, R. J. (1997) *Nature Med.* 3:1233–1241.
2. Chinery, R., Beauchamp, R. D., Shyr, Y., Kirkland, S. C., Coffey, R. J., and Morrow, J. D. (1998) *Cancer Res.* 58:2323–2327.
3. Nobel, C. S. I., Kimland, M., Lind, B., Orrenius, S., and Slater, A. F. G. (1995) *J. Biol. Chem.* 270:26202–26208.
4. Verhaegh, G. W., Richard, M. -J., and Hainaut, P. (1997) *Mol. Cell. Biol.* 17:5966–5706.
5. Burkitt, M. J., Bishop, H. S., Milne, L., Tsang, S. Y., Provan, G. J., Nobel, C. S. I., Orrenius, S., and Slater, A. F. G. (1998) *Archiv. Biochem. Biophys.* 353:73–84.
6. Hirst, S. J., Barnes, P. J., and Twort, C. H. C. (1992) *Am. J. Respir. Cell Mol. Biol.* 7:574–581.
7. Dashtaki, R., Whorton, A. R., Murphy, T. M., Chitano, P., Reed, W., and Kennedy, T. P. (1998) *J. Pharmacol. Exper. Ther.* 285:876–219.
8. Royall, J. A., and Ischiropoulos, H. (1993) *Archiv. Biochem. Biophys.* 302:348–355.
9. Anderson, M. E. (1985) *Methods Enzymol.* 113:548–555.
10. Brar, S. S., Kennedy, T. P., Whorton, A. R., Murphy, T. M., Chitano, P., and Hoidal, J. R. (1999) *J. Biol. Chem.* 274:20017–20026.
11. Kennedy, T., Ghio, A. J., Reed, W., Samet, J., Zagorski, J., Quay, J., Carter, J., Dailey, L., Hoidal, J. R., and Devlin, R. B. (1998) *Am. J. Respir. Cell Mol. Biol.* 19:366–378.
12. Faiman, M. D., Jensen, J. C., and Lacoursiere, R. B. (1984) *Clin. Pharmacol. Ther.* 36:520–526.
13. Liu, B., and Hannun, Y. A. (1997) *J. Biol. Chem.* 272:16281–16287.
14. Liu, B., Andrieu-Abadie, N., Levade, T., Zhang, P., Obeid, L. M. and Hannun, Y. A. (1998) *J. Biol. Chem.* 273:11313–11320.
15. Jayadev, S., Liu, B., Bielawska, A. E., Lee, J. Y., Nazaire, F., Pushkareva, M. Y., Obeid, L. M. and Hannyn, Y. A. (1995) *J. Biol. Chem.* 270:2047–2052.
16. Gordge, M. P., Meyer, D. J., Hothersall, J., Neild, G. H., Payne, N. N., and Noronha-Dutra, A. (1995) *Brit. J. Pharmacol.* 114:1083–1089.
17. Gorren, A. C. F., Schrammel, A., Schmidt, K., and Mayer, B. (1996) *Archiv. Biochem. Biophys.* 330:219–2238.
18. Arnelle, D. R., Day, B. J., and Stamler, J. S. (1997) Nitric Oxide: *Biol. and Chem.* 1:56–64.
19. Shen, Y. H., Wang., X. L., and Wilcken, D. E. L. (1998) *FEBS Lett.* 433:125–131.
20. Hortelano, S., Dallaporta, B., Zamzami, N., Hirsch, T., Susin, S. A., Marzo, I., Bosca, L., and Droemer, G. (1997) *FEBS Lett.* 410:373–377.
21. Sylvester, A. M., Chen, D., Krasinski, K., and Andres, V. (1998) *J. Clin. Invest.* 101:940–948.
22. Brewer, G. J., Yuzbasiyan-Gurkan, V., and Lee, D. Y. (1990) *J. Am. Coll. Nutr.* 9:487–491.
23. Reeves, P. G., Briske-Anderson, M., and Newman, S. M., Jr. (1996) *J. Nutr.* 126:1701–1712.
24. Burns, R. P., McCullough, F. P., and McAuliffe, C. A. (1980) *Adv. Inorg. Chem. Radiochem.* 23:211–280.
25. Schreck, R., Meier, B., Mannel, D. N., Droge, W., and Baeuerle, P. A. (1992) *J. Exp. Med.* 175:1181–1194.
26. Brennan, P., and O'Neill, L. A. (1996) *Biochem. J.* 320:975–981.
27. Galter, D., Mihm, S., and Droge, W. (1994) *Eur. J. Biochem.* 221:639–648.
28. Nobel, C. S. I., Kimland, M., Nicholson, D. W., Orrenius, S., and Slater, A. F. G. (1997) *Chem. Res. Toxicol.* 10:1319–1324.
29. Nobel, C. S. I., Burgess, D. H., Zhivotovsky, B., Burkitt, M. J., Orrenius, S. and Slater, A. F. G. (1997) *Chem. Res. Toxicol.* 10:636–643.

30. McConkey, D. J., and Orrenius, S. (1994) *Trends Cell Biol.* 4:370–375.
31. Simizu, S., Takada, M., Umezawa, K., and Imoto, M. (1998) *J. Biol. Chem.* 273:26900–26907.
32. Denke, S. J., Harford, P. H., Lee, K. -Y., Denke, C. F., Wright, S. E., and Jenkinson, S. G. (1997) *Am. J. Respir. Cell Mol. Biol.* 17:227–234.
33. Richards, J. P., Bachinger, H. P., Goodman, R. H., and Brennan, R. G. (1996) *J. Biol. Chem.* 271:13716–13723.
34. Klatt, P., Molina, E. P., and Lamas, S. (1999) *J. Biol. Chem.* 274:15857–15864.
35. Brown, J. R., Nigh, E., Lee, R. J., Ye, H., Thompson, M. A., Saudou, F., Pestell, R. G., and Greenberg, M. E. (1998) *Mol. Cell. Biol.* 18:5609–5619.
36. Borovansky, J., Blasko, M., Siracky, J., Schothorst, A. A., Smit, N. P. M., and Pavel, S. (1997) *Melanoma Res.* 7:449–453.
37. Iguchi, K., Hamatake, M., Ishida, R., Usami, Y., Adachi, T., Yamamoto, H., Koshida, K., Uchibayashi, T., and Hirano, K. (1998) *Eur. J. Biochem.* 253:766–770.
38. Soignet, S. L., Maslak, P., Wang, Z. G., Jhanwar, S., Calleja, E., Dardashti, L. J., Corso, D., DeBlasio, A., Gabrilove, J., Scheinberg, D. A., Pandolfi, P. P., and Warrell, R. P., Jr. (1998) *N. Engl. J. Med.* 339:1389–1391.
39. Connell, P., Young, V. M., Toborek, M., Cohen, D. A., Barve, S., McClain, C. J., and Hennig, B. (1997) *J. Am. Coll. Nutr.* 5:411–417.
40. Shumilla, J. A., Wetterhanm, K. E., and Barchowsky, A. (1998) *Archiv. Biochem. Biophys.* 349:346–362.
41. Yang, J. P., Merin, J. P., Nakano, T., Kato, T., Itade, Y., and Okamoto, T. (1995) *FEBS Lett.* 361:89–96.
42. Handel, M. L., Watts, C. K. W., DeFazio, A., Day, R. O., and Sutherland, R. L. (1995) *Proc. Natl. Acad. Sci. USA* 92:4496–4501.
43. Halliwell, B., and Gutteridge, J. M. C. (1990) *Methods Enzymol.* 186:1–85.
44. Percival, S. S., and Harris, E. D. (1990) *Am. J. Physiol.* 258:3140–3146.

That which is claimed is:

1. A method for treating an established cancer sensitive to the enhanced combination of tetraalkyl thiuram disulfide and a heavy metal ion comprising administering said combination to a mammal in a therapeutically effective amount and wherein the heavy metal ion is a copper ion.

2. The method of claim 1, wherein said tetraalkyl thiuram disulfide is tetraethyl thiuram disulfide.

3. The method of claim 1, wherein the thiuram disulfide and the heavy metal ion are administered orally.

4. The method of claim 1, wherein said thiuram disulfide and said heavy metal ion are administered intravenously.

5. The method of claim 1, wherein said thiuram disulfide is administered a dosage of from about 125 to about 1000 mg.

6. The method according to claim 1, wherein said established cancer is melanoma, lung cancer, breast cancer, or prostatic carcinoma.

* * * * *